US008563028B2

(12) United States Patent
Sullivan et al.

(10) Patent No.: US 8,563,028 B2
(45) Date of Patent: Oct. 22, 2013

(54) OPHTHALMIC DEVICE, AND METHOD OF USE THEREOF, FOR INCREASING OCULAR BOUNDARY LUBRICATION

(75) Inventors: Benjamin Sullivan, San Diego, CA (US); Tannin A. Schmidt, Calgary (CA); David A. Sullivan, Boston, MA (US)

(73) Assignees: The Regents of the University of California, Oakland, CA (US); Schepens Eye Research Institute, Boston, MA (US)

( * ) Notice: Subject to any disclaimer, the term of this patent is extended or adjusted under 35 U.S.C. 154(b) by 65 days.

(21) Appl. No.: 12/940,454

(22) Filed: Nov. 5, 2010

(65) Prior Publication Data

US 2011/0142908 A1 Jun. 16, 2011

Related U.S. Application Data

(63) Continuation of application No. PCT/US2009/043018, filed on May 6, 2009.

(60) Provisional application No. 61/051,112, filed on May 7, 2008.

(51) Int. Cl.
*A61K 9/00* (2006.01)
*A61K 47/00* (2006.01)

(52) U.S. Cl.
USPC ................... 424/429; 424/423; 424/279.1

(58) Field of Classification Search
None
See application file for complete search history.

(56) References Cited

U.S. PATENT DOCUMENTS

| | | | | |
|---|---|---|---|---|
| 4,801,619 A * | 1/1989 | Lindblad | | 514/42 |
| 4,964,206 A | 10/1990 | Knoll et al. | | |
| 5,286,829 A * | 2/1994 | Fedorov et al. | | 527/201 |
| 5,326,558 A | 7/1994 | Turner et al. | | |
| 5,351,100 A | 9/1994 | Schwenzfeier et al. | | |
| 5,620,921 A | 4/1997 | Sullivan | | |
| 5,688,765 A | 11/1997 | Sullivan | | |
| 5,702,456 A | 12/1997 | Pienkowski | | |
| 5,942,558 A * | 8/1999 | Korb | | 523/106 |
| 6,107,289 A | 8/2000 | Sullivan | | |
| 6,433,142 B1 | 8/2002 | Turner et al. | | |
| 6,635,267 B1 | 10/2003 | Miyoshi et al. | | |
| 6,689,748 B1 | 2/2004 | Theoharides | | |
| 6,743,774 B1 | 6/2004 | Jay | | |
| 6,815,074 B2 * | 11/2004 | Aguado et al. | | 428/447 |
| 6,940,580 B2 * | 9/2005 | Winterton et al. | | 351/159.33 |
| 6,960,562 B2 | 11/2005 | Jay | | |
| 7,014,860 B1 * | 3/2006 | Kawata et al. | | 424/422 |
| 7,030,223 B2 | 4/2006 | Turner et al. | | |
| 7,329,415 B2 * | 2/2008 | Lally et al. | | 424/429 |
| 7,361,738 B2 | 4/2008 | Turner et al. | | |
| 7,811,267 B2 * | 10/2010 | Norrby et al. | | 604/289 |
| 2003/0008154 A1 * | 1/2003 | Aguado et al. | | 428/447 |
| 2003/0130324 A1 * | 7/2003 | McAvoy et al. | | 514/360 |
| 2003/0219909 A1 * | 11/2003 | Lally et al. | | 436/518 |
| 2004/0009893 A1 | 1/2004 | Wang et al. | | |
| 2004/0029913 A1 | 2/2004 | Dalton et al. | | |
| 2004/0157073 A1 * | 8/2004 | Burrell et al. | | 428/500 |
| 2005/0063996 A1 | 3/2005 | Peyman | | |
| 2005/0129778 A1 | 6/2005 | Mulye | | |
| 2005/0196370 A1 | 9/2005 | Yu et al. | | |
| 2005/0287223 A1 * | 12/2005 | Peyman | | 424/582 |
| 2006/0067927 A1 | 3/2006 | Chandrasekaran | | |
| 2006/0228394 A1 * | 10/2006 | Peyman | | 424/427 |
| 2006/0281739 A1 * | 12/2006 | Gadek et al. | | 514/227.5 |
| 2007/0031471 A1 | 2/2007 | Peyman | | |
| 2007/0191268 A1 | 8/2007 | Flannery et al. | | |
| 2007/0249557 A1 | 10/2007 | Jay | | |
| 2007/0264226 A1 | 11/2007 | Karagoezian et al. | | |
| 2007/0275032 A1 * | 11/2007 | Wimmer et al. | | 424/423 |
| 2007/0292496 A1 | 12/2007 | Herrero Vanrell et al. | | |
| 2008/0053845 A1 | 3/2008 | Newman | | |
| 2008/0076829 A1 | 3/2008 | Dalton | | |
| 2008/0094573 A1 * | 4/2008 | Vermette et al. | | 351/177 |
| 2008/0097606 A1 | 4/2008 | Cragg et al. | | |
| 2008/0197324 A1 | 8/2008 | Zhao et al. | | |

(Continued)

FOREIGN PATENT DOCUMENTS

WO 94/06485 A1 3/1994
WO WO94/06485 A1 3/1994

(Continued)

OTHER PUBLICATIONS

Zappone et al., 2007, "Adsorption, Lubrication, and Wear of Lubricin on Model Surfaces: Polymer Brush-Like Behavior of a Glycoprotein," Biophysical Journal, 92:1693-1708.
Supplementary European Search Report for EP 09 74 3589 mailed Oct. 31, 2011.
International Search Report for PCT/US2010/53797 dated Jan. 6, 2011 (2 pages).
Disclosure under 37 C.F.R. 1.56 (2 pages).
International PCT Search Report for PCT/US2009/043018 dated Jun. 16, 2009.

(Continued)

*Primary Examiner* — Robert A Wax
*Assistant Examiner* — Olga V Tcherkasskaya
(74) *Attorney, Agent, or Firm* — Sutherland Asbill & Brennan LLP

(57) ABSTRACT

The present invention provides an ophthalmic device, and method of use thereof, for an individual wearing an ophthalmic lens to increase ocular surface boundary lubrication. The invention device comprises an ophthalmic lens and a sacrificial mechanism disposed on the ophthalmic lens, wherein the sacrificial mechanism comprises a plurality of surface bound receptors, such as PRG4, hyaluronic acid, and DNA aptamers, that reversibly bound to a lubricating composition comprising a gel forming agent, a surfactant, or a combination thereof, effectively inhibiting or preventing protein and lipid adsorption on the surface of the lens, and mitigate shear stress and reduce the friction between the lens and the ocular surface of the individual in need.

13 Claims, 10 Drawing Sheets

(56) References Cited

U.S. PATENT DOCUMENTS

| | | | |
|---|---|---|---|
| 2008/0213274 A1* | 9/2008 | Sabbadini et al. | ......... 424/141.1 |
| 2009/0060933 A1 | 3/2009 | Estell et al. | |
| 2009/0068247 A1 | 3/2009 | Jay | |
| 2009/0160074 A1 | 6/2009 | Pruitt et al. | |
| 2010/0092452 A1 | 4/2010 | Sullivan | |
| 2011/0059902 A1 | 3/2011 | Sullivan | |
| 2011/0070222 A1 | 3/2011 | Sullivan | |
| 2012/0321611 A1 | 12/2012 | Sullivan | |

FOREIGN PATENT DOCUMENTS

| | | | |
|---|---|---|---|
| WO | 00/27421 | A2 | 5/2000 |
| WO | WO 03030941 | A1 * | 4/2003 |
| WO | WO03/057270 | A1 | 7/2003 |
| WO | WO 03057270 | A1 * | 7/2003 |
| WO | 2004/035736 | A2 | 4/2004 |
| WO | 2005016130 | | 2/2005 |
| WO | WO 2005027933 | A1 * | 3/2005 |
| WO | WO 2005110473 | A2 * | 11/2005 |
| WO | 2006/094026 | A1 | 9/2006 |

OTHER PUBLICATIONS

Foulks, 2006, "Pharmacological Management of Dry Eye in the Elderly Patient," Therapy in Practice, 25(2):105-118.
Japanese Office Action dated Nov. 20, 2012 for Japanese Application No. 2011-508534.
Japanese Office Action dated Nov. 20, 2012 for Japanese Application No. 2011-508633.
Japanese Office Action dated Nov. 20, 2012 for Japanese Application No. 2011-508634.
Jay et al. "Prevention of cartilage degeneration and restoration of chrondroprotection by lubricin tribosupplementation in the rat following anterior cruciate ligament transection" Arthritis Rheum. Aug. 2010;62(8):2382-91.
Written Opinion for PCT/US09/43018 dated Jun. 16, 2009 (5 pages).

* cited by examiner

U 5th Min

OPHTHALMIC DEVICE, AND METHOD OF USE THEREOF, FOR INCREASING OCULAR BOUNDARY LUBRICATION

CROSS-REFERENCE TO RELATED APPLICATIONS

This patent application is a continuation of PCT Application No. PCT/US09/043,018, filed May 6, 2009, which claims priority benefit of U.S. Provisional Application No. 61/051,112 filed May 7, 2008, each of which is incorporated herein by reference in their entireties.

GOVERNMENT SUPPORT

This invention was made with government support under EY05612 awarded by the National Institute of Health. The government has certain rights in the invention.

FIELD OF THE INVENTION

The present invention relates to an ophthalmic device for the management of ocular lubrication in the presence of an ophthalmic lens.

BACKGROUND

The proteoglycan 4 (prg4) gene encodes for highly glycosylated proteins termed megakaryocyte stimulating factor (MSF), lubricin, and superficial zone protein (SZP) (1). These molecules are collectively referred to as PRG4 or PRG4 proteins. PRG4 is present in synovial fluid and at the surface of synovium (2), tendon (3), and meniscus (4) and is suspected as being an important component for healthy synovial joints. See, e.g., (5), (6).

In tissues such as synovial joints, physicochemical modes of lubrication have been classified as fluid film or boundary. The operative lubrication modes depend on the normal and tangential forces on the articulating tissues, on the relative rate of tangential motion between these surfaces, and on the time history of both loading and motion. The friction coefficient, $\mu$, provides a quantitative measure, and is defined as the ratio of tangential friction force to the normal force. One type of fluid-mediated lubrication mode is hydrostatic. At the onset of loading and typically for a prolonged duration, the interstitial fluid within cartilage becomes pressurized, due to the biphasic nature of the tissue; fluid may also be forced into the asperities between articular surfaces through a weeping mechanism. Pressurized interstitial fluid and trapped lubricant pools may therefore contribute significantly to the bearing of normal load with little resistance to shear force, facilitating a very low $\mu$. Also, at the onset of loading and/or motion, squeeze film, hydrodynamic, and elastohydrodynamic types of fluid film lubrication occur, with pressurization, motion, and deformation acting to drive viscous lubricant from and/or through the gap between two surfaces in relative motion.

The relevant extent to which fluid pressure/film versus boundary lubrication occurs classically depends on a number of factors (13). When lubricant film can flow between the conforming sliding surfaces, which can deform elastically, elastohydrodynamic lubrication occurs. Pressure, surface roughness, and relative sliding velocity determine when full fluid lubrication begins to break down and the lubrication enters new regimes. As velocity decreases further, lubricant films adherent to the articulating surfaces begin to contribute and a mixed regime of lubrication occurs. If the velocity decreases even further and only an ultra-thin lubricant layer composed of a few molecules remain, boundary lubrication occurs. A boundary mode of lubrication is therefore indicated by a friction coefficient (ratio of the measured frictional force between two contacting surfaces in relative motion to the applied normal force) during steady sliding being invariant with factors that influence formation of a fluid film, such as relative sliding velocity and axial load (14). For articular cartilage, it has been concluded boundary lubrication is certain to occur, although complemented by fluid pressurization and other mechanisms (15-18).

In boundary lubrication, load is supported by surface-to-surface contact, and the associated frictional properties are determined by lubricant surface molecules. This mode has been proposed to be important because the opposing cartilage layers make contact over ~10% of the total area, and this may be where most of the friction occurs (19). Furthermore, with increasing loading time and dissipation of hydrostatic pressure, lubricant-coated surfaces bear an increasingly higher portion of the load relative to pressurized fluid, and consequently, this mode can become increasingly dominant (13, 20). Boundary lubrication, in essence, mitigates stick-slip (13), and is therefore manifest as decreased resistance both to steady motion and the start-up of motion. The latter situation is relevant to load bearing articulating surfaces after prolonged compressive loading (e.g., sitting or standing in vivo) (21). Typical wear patterns of cartilage surfaces (22) also suggest that boundary lubrication of articular cartilage is critical to the protection and maintenance of the articular surface structure.

With increasing loading time and dissipation of hydrostatic pressure, lubricant-coated surfaces bear an increasingly higher portion of the load relative to pressurized fluid, and consequently, $\mu$ can become increasingly dominated by this mode of lubrication. A boundary mode of lubrication is indicated by values of $\mu$ during steady sliding being invariant with factors that influence formation of a fluid film, such as relative sliding velocity and axial load. Boundary lubrication, in essence, mitigates stickslip, and is therefore manifest as decreased resistance both to steady motion and the start-up of motion.

The precise mechanisms of boundary lubrication at biological interfaces are currently unknown. However, proteoglycan 4 (PRG4) may play a critical role as a boundary lubricant in articulating joints. This secreted glycoprotein is thought to protect cartilaginous surfaces against frictional forces, cell adhesion and protein deposition. Various native and recombinant lubricin proteins and isoforms have been isolated and characterized. For instance, U.S. Pat. Nos. 5,326,558; 6,433,142; 7,030,223, and 7,361,738 disclose a family of human megakaryocyte stimulating factors (MSFs) and pharmaceutical compositions containing one or more such MSFs for treating disease states or disorders, such as a deficiency of platelets. U.S. Pat. Nos. 6,960,562 and 6,743,774 also disclose a lubricating polypeptide, tribonectin, comprising a substantially pure fragments of MSF, and methods of lubricating joints or other tissues by administering tribonectin systemically or directly to tissues.

A challenge to boundary lubrication is the presence of inflammation in surrounding tissues, as well as increased protease levels in the synovial fluid. Loss of the boundary-lubricating ability of synovial fluid after injury is associated with damage to the articular cartilage matrix. This can be attributed to inflammatory processes resulting from the injury, particularly in the early phases. Another challenge to boundary lubrication is a sex steroid imbalance, especially in arthritic disorders such as rheumatoid arthritis. Sex steroids are involved in the pathogenesis and regulation of inflammation in rheumatoid arthritis, a disease characterized by chronic inflammatory synovitis. Androgens suppress, whereas estrogens promote, inflammatory processes. Consequently, the relative levels of androgens and estrogens in the synovial environment are extremely important in determining the progression of inflammation (7, 8, 23). Various androgen compounds reduce the magnitude of lymphocyte infiltration in lacrimal tissue. See, e.g., U.S. Pat. Nos. 5,620,921; 5,688,765; 5,620,921; and 6,107,289.

Engineering of contact lens surfaces have traditionally focused on increasing oxygen transport. Recent advances in contact lens chemistries have also focused on increasing water content and hydrophilicity to inhibit protein deposition on the lens surface. Protein deposition on the posterior/inner surface of the contact lens surfaces has been implicated as a causative factor in the corneal abrasions and mechanical trauma associated with contact lens wear.

Advances in silicone hydrogel materials have gained popularity due to their ability to reduce protein absorption through increased hydrophilicity. Examples include Lotrafilcon A (N,N-dimethylacrylamide, trimethylsiloxy silane and siloxane monomer, CIBA Vision, a.k.a. Focus NIGHT & DAY, 24% water content, 175 Dk/t $O_2$ transmissibility), Lotrafilcon B (N,N-dimethylacrylamide, trimethylsiloxy silane and siloxane monomer, CIBA Vision, a.k.a. $O_2$ Optix, 33% water content, 138 Dk/t $O_2$ transmissibility), Balafilcon (N-vinyl pyrrolidone, tris-(trimethylsiloxysilyl) propylvinyl carbamate, N-carboxyvinyl ester, poly(dimethysiloxy) di(silylbutanol)bis(vinyl carbamate), Bausch & Lomb, a.k.a. PureVision, 36% water content, 101 Dk/t $O_2$ transmissibility), Galyfilcon A (monofunctional polydimethylsiloxane, dimethylacrylamide, poly-2-hydroxyethyl methacrylate, siloxane monomer, polyvinyl pyrrolidone, ethyleneglycol dimethacrylate, Johnson & Johnson Vision Care, a.k.a. ACUVUE Advance, 47% water content, 86 Dk/t $O_2$ transmissibility), Etafilcon AA (poly-2-hydroxyethyl methacrylate, methacrylic acid, Johnson & Johnson Vision Care, a.k.a. ACUVUE 2, 58% water content, 21 Dk/t $O_2$ transmissibility). In addition to the material choices, these silicone hydrogel lenses are also manufactured with an additional treatment steps to improve hydrophilicity. For example, Lotrafilcon A & B use plasma coating, Balafilcon A makes use of a plasma oxidation process, and ACUVUE Advance lenses include polyvinyl pyrrolidone as an internal wetting agent [25]. Plasma treatments are known to fade and lose efficacy over time.

Protein adsorption at contact lens surfaces is commonly attributed to human albumin and lysozyme, two of the most abundant proteins in the tear film. Conflicting results have been reported regarding the water content, hydrophobicity, charge, pore size and surface roughness. Because the isoelectric points of albumin and lysozyme are on opposite ends of the pH of human tear, the minimum protein adsorption seems to occur when charge, water content and hydrophilicity are properly balanced. Lower water content materials tend to bind albumin while higher water content materials tend to bind lysozyme [24]. Luensmann et. al. [24] also indicated that silicone hydrogels exhibit both hydrophobic and hydrophilic domains; and following evaporation, chain rotation forces tend to expose hydrophobic domains to the air, thereby increasing the chance for dry spots. Polar lipids may also bind to hydrophilic regions on the lens surface, resulting in exposed hydrophobic tails, which may also promote dry spots.

Hyperosmolarity is a common result of contact lens wear. Those with a reduced quantity or quality of lipid production tend to exhibit drastically less stable tear films, and the presence of a contact lens may exacerbate the instability. This leads to a faster evaporation of the tear film, and a concentration of the tears over the ocular surface.

SUMMARY OF THE INVENTION

The present invention provides, in various embodiments, an ophthalmic device for the management of ocular lubrication in the presence of an ophthalmic lens. Given the relationship between osmotic pressure and the electromechanical interactions within charged molecules, the present invention provides for the methods of managing decreased ocular boundary lubrication in ophthalmic lens wear by modulating hyperosmolarity at the ocular surface. In certain instances, by interrupting the feedback mechanisms which promote hyperosmolarity, the integration of a sacrificial mechanism into the pre- and/or postocular ophthalmic lens reduces the static and kinetic friction coefficient at the ocular surface during an eyelid blink. In some instances, over time, the reduction in shear stress alleviates hyperosmolarity driven by the gain of this feedback mechanism.

Described in certain embodiments of the present invention is a sacrificial mechanism disposed on at least a portion of the inner surface in an amount effective to provide ocular boundary lubrication in an individual wearing the ophthalmic lens. In one embodiment of the current invention, the sacrificial mechanism comprises a plurality of lubricating surface bound receptors, such as plurality of PRG4 (i.e., a plurality of PRG4 molecules). In this embodiment, the lubricating surface bound receptor (e.g., PRG4) is allowed to interact with endogenous proteins and proteoglycans within the tear film to facilitate activation of the sacrificial mechanism. In some instances, this interaction prevents or inhibits protein or lipid adsorption at the lens surface, reduce dry spots on the lens, and reduce the friction between the lens and the ocular surface. In preferred embodiments, the PRG4 has an average molar mass of between 50 kDa and 400 kDa, and is recombinant PRG4, isolated naturally-occurring PGR4, or a functional fragment thereof.

In some embodiments, the ophthalmic device of the current invention further comprises a lubricating composition associated with or otherwise reversibly bound to surface active receptor(s) (e.g., PRG4) or surface of the opthalmic lens. In certain embodiments, the lubricating composition described in the current invention comprises a gel forming agent or composition and/or a surfactant or surfactant composition, or a combination thereof. In one embodiment, the gel forming agent or composition comprises hyaluronic acid or sodium hyaluronate. In another embodiment, the surfactant or surfactant composition comprises one or more surface active phospholids, such as L-α-dipalmitoylphosphatidylcholine, phosphatidylcholine, phosphatidylethanolamine, and sphingomyelin. Described in certain embodiments of the present invention is the observation that the gel forming or surfactant agent or composition associated with the boundary lubricant molecules detach during a shear event, thereby preventing the shear stress from reaching the epithelial surface. Following the transient shearing event, the gel forming and/or surfactant agent or composition, allowed to return to their undisturbed equilibrium, rebind to the surface bound receptors and increase the probability of release from the receptor with increasing shear amplitude, such that any one association is easily reversible.

In further or alternative embodiments, the surface bound receptors comprise hyaluronic acid. In this embodiment, the ophthalmic device of the current invention further comprises a lubricating agent or composition associated with, or otherwise reversibly bound to, the hyaluronic acid. The lubricating composition in this embodiment, comprises a gel forming composition comprising PRG4, and/or a surfactant composition comprising one or more surface active phospholipids, such as L-α-dipalmitoylphosphatidylcholine, phosphatidylcholine, phosphatidylethanolamine, and sphingomyelin.

In certain other embodiments, the surface bound receptors comprise DNA aptamers. DNA aptamers that may be utilized herein include those that recognize proteoglycans such as PRG4, hyaluronic acid, long chain sugars such as dextrans, polyethylene glycols, or other DNA constructs, and feature tunable affinity through an iterative evolutionary selection, or through ratiometric design against a semi-complementary hybrid (i.e., a purposefully mismatched polyG-A-polyG could act as a surface bound receptor for a polyG-T-polyG strand, with shortening lengths of polyG increasing relative affinity).

In some embodiments, the sacrificial mechanism (e.g., comprising surface bound receptor(s)) is bound to the ophthalmic lens by reversible and/or irreversible interactions (e.g., covalent bonds, non-covalent interactions, or the like). In certain embodiments, the present invention provides that the surface bound receptors are adhered to the ophthalmic lens surface by direct adsorption, hydrophobic ionic, or covalent binding or by linker chemistries selected from the group consisting of homo- or hetero-bifunctional linkers, N-hydroxy succinimidyl esters, biotin, avidin, streptavidin, maleimide, thiol bonding, amines, hydrazones, dendrimers, and carbodiimides.

Provided in certain embodiments herein is an ophthalmic device comprising an ophthalmic lens with an outer surface and an inner surface, PRG4, a PRG4 inducing compound, or a combination thereof being associated with at least a portion of the outer or inner surface in an amount effective to provide ocular boundary lubrication in an ocular environment of an individual wearing the ophthalmic lens. In some embodiments, the PRG4 is associated in a manner so as to provide a sacrificial mechanism, as described herein. In certain embodiments, the PRG4 is bound to the surface of the ophthalmic lens. In some embodiments, a device described herein comprises a lubricating composition disposed on the surface of the ophthalmic lens, the lubricating composition comprising (i) a gel-forming agent, a surfactant, or a combination thereof; and (ii) optionally PRG4.

In some embodiments, lubricating, gel forming or surfactant composition further comprises one or more ophthalmically acceptable agents selected from the group consisting of an ophthalmically acceptable demulcent, ophthalmically acceptable excipient, ophthalmically acceptable astringent, ophthalmically acceptable vasoconstrictor, and ophthalmically acceptable emollient. Exemplary ophthalmically acceptable demulcents contemplated in the present invention include, but are not limited to, carboxymethylcellulose sodium (e.g., about 0.2 to 2.5% w/v), hydroxyethyl cellulose (e.g., about 0.2 to 2.5% w/v), hypromellose (e.g., about 0.2 to 2.5% w/v), methylcellulose (e.g., about 0.2 to 2.5% w/v), dextran 70 (e.g., about 0.1% w/v), gelatin (e.g., about 0.01% w/v), glycerin (e.g., about 0.2 to 1% w/v), polyethylene glycol 300 (e.g., about 0.2 to 1% w/v), polyethylene glycol 400 (e.g., about 0.2 to 1% w/v), polysorbate 80 (e.g., about 0.2 to 1% w/v), propylene glycol (e.g., about 0.2 to 1% w/v), polyvinyl alcohol (e.g., about 0.1 to 4% w/v), povidone (e.g., about 0.1 to 2% w/v).

Exemplary ophthalmically acceptable excipients/emollients contemplated in the present invention include, but are not limited to, anhydrous lanolin (e.g., about 1 to 10% w/v), lanolin (e.g., about 1 to 10% w/v), light mineral oil (e.g., ≤about 50% w/v), mineral oil (e.g., ≤about 50% w/v), paraffin (e.g., ≤about 5% w/v), petrolatum (e.g., ≤about 100% w/v), white ointment (e.g., ≤about 100% w/v), white petrolatum (e.g., ≤about 100% w/v), white wax (e.g., ≤about 5% w/v), yellow wax (e.g., ≤about 5% w/v). An exemplary ophthalmically acceptable astringent contemplated in the present invention includes, but is not limited to, zinc sulfate (e.g., about 0.25% w/v). Exemplary ophthalmically acceptable vasoconstrictors contemplated in the present invention include, but are not limited to, ephedrine hydrochloride (e.g., about 0.123% w/v), naphazoline hydrochloride (e.g., about 0.01 to about 0.03% w/v), phenylephrine hydrochloride (e.g., about 0.08 to about 0.2% w/v), and tetrahydrozoline hydrochloride (e.g., about 0.01 to about 0.05% w/v).

In some of these embodiments, the demulcents, excipients, astringents, vasoconstrictors, emollients and electrolytes provide a means to deliver the boundary lubricant molecules in an ophthalmically acceptable manner. Ophthalmically acceptable compositions are suitable for topical application to the ocular surface if they lack unacceptable eye toxicity, burning, itchiness, viscosity, blurred vision, etc. upon application.

In certain embodiments, the gel forming or surfactant composition further comprises other ophthalmic lens care compounds that may be suspended in a phosphate buffered saline or an osmotically balanced salt solution of tear electrolytes, including one or more of sodium chloride (e.g., about 44% to 54% mole fraction), potassium chloride (e.g., about 8% to 14% mole fraction), sodium bicarbonate (e.g., about 8% to 18% mole fraction), potassium bicarbonate (e.g., about 0% to 4% mole fraction), calcium chloride (e.g., about 0% to 4% mole fraction), magnesium chloride (e.g., about 0% to 4% mole fraction), trisodium citrate (e.g. about 0% to 4% mole fraction), and hydrochloric acid (e.g., about 0% to 20% mole fraction) or sodium hydroxide (e.g., about 0% to 20% mole fraction). In one embodiment, the carrier could be formulated to generate an aqueous electrolyte solution in the 150-200 mM range.

In certain embodiments, the ophthalmic lens care compounds are suspended in an ophthalmically acceptable balanced salt solution comprising at least three electrolytes, including but not limited to, sodium chloride (NaCl) 0.64%, potassium chloride (KCl) 0.075%, calcium chloride dihydrate ($CaCl_2.2H_2O$) 0.048%, magnesium chloride hexahydrate ($MgCl_2.6H_2O$) 0.03%, sodium acetate trihydrate ($C_2H_3NaO_2.3H_2O$) 0.39%, sodium citrate dehydrate ($C_6H_5Na_3O_7.2H_2O$) 0.17%, sodium hydroxide and/or hydrochloric acid (to adjust pH to approximately 7.5) with an osmolarity of approximately 300 mOsms/L.

In certain embodiments, the ophthalmic lens Care compounds are suspended in an ophthalmically acceptable balanced salt solution, comprised of sodium (Na+) of approximately 128 mM, potassium (K+) of approximately 24 mM, chloride (Cl−) of approximately 113 mM, calcium (Ca2+) of approximately 0.4 mM, magnesium (Mg2+) of approximately 0.3 mM, HCO3− of approximately 5 mM, citrate of approximately 1 mM, phosphate of approximately 14 mM, acetate of approximately 15 mM, and sodium hydroxide and/or hydrochloric acid (to adjust pH to approximately 7.5) with an osmolarity of approximately 300 mOsms/L.

The present invention also provides an ophthalmic device comprising an ophthalmic lens with an outer surface and an inner surface and an ocular boundary lubricant composition disposed on at least a portion thereof one or more ocular boundary lubricating agent, such as, by way of non-limiting example, of PRG4, a PGR4 inducer, hyaluronic acid, sodium hyaluronate, and/or a phospholipid (e.g., in an amount effective to provide, alone or in combination with the surface bound receptor, ocular boundary lubrication in an individual wearing the ophthalmic lens). In some embodiments, a gel-forming or surfactant composition utilized herein comprises, a gel forming agent and/or a surfactant, and an optional ocular boundary lubricating agent, such as, by way of non-limiting example, PRG4, a PGR4 inducer, hyaluronic acid, sodium hyaluronate, and/or a phospholipid (preferably present in an amount effective to provide, alone or in combination with the surface bound receptor, ocular boundary lubrication in an individual wearing the ophthalmic lens). Also provided in certain embodiments therein is a method for providing ocular boundary lubrication to an individual in need thereof by applying to an eye of the individual an ophthalmic device of the present invention. In some instances, the invention method provides a sacrificial mechanism on the ophthalmic lens to mitigate shear stress, so as to treat ocular surface hyperosmolarity.

DETAILED DESCRIPTION OF THE INVENTION

Provided herein, are ophthalmic devices and methods for managing ocular boundary lubrication in association with ophthalmic lens wear. In certain embodiments, the invention modulates hyperosmolarity at the ocular surface via a sacrificial mechanism to improve ocular boundary lubrication. Provided herein is an ophthalmic device comprising an ophthalmic lens with an outer surface and an inner surface and a sacrificial mechanism disposed on at least a portion thereof in an amount effective to provide ocular boundary lubrication in an ocular environment in an individual wearing the ophthalmic lens.

Figure 1:
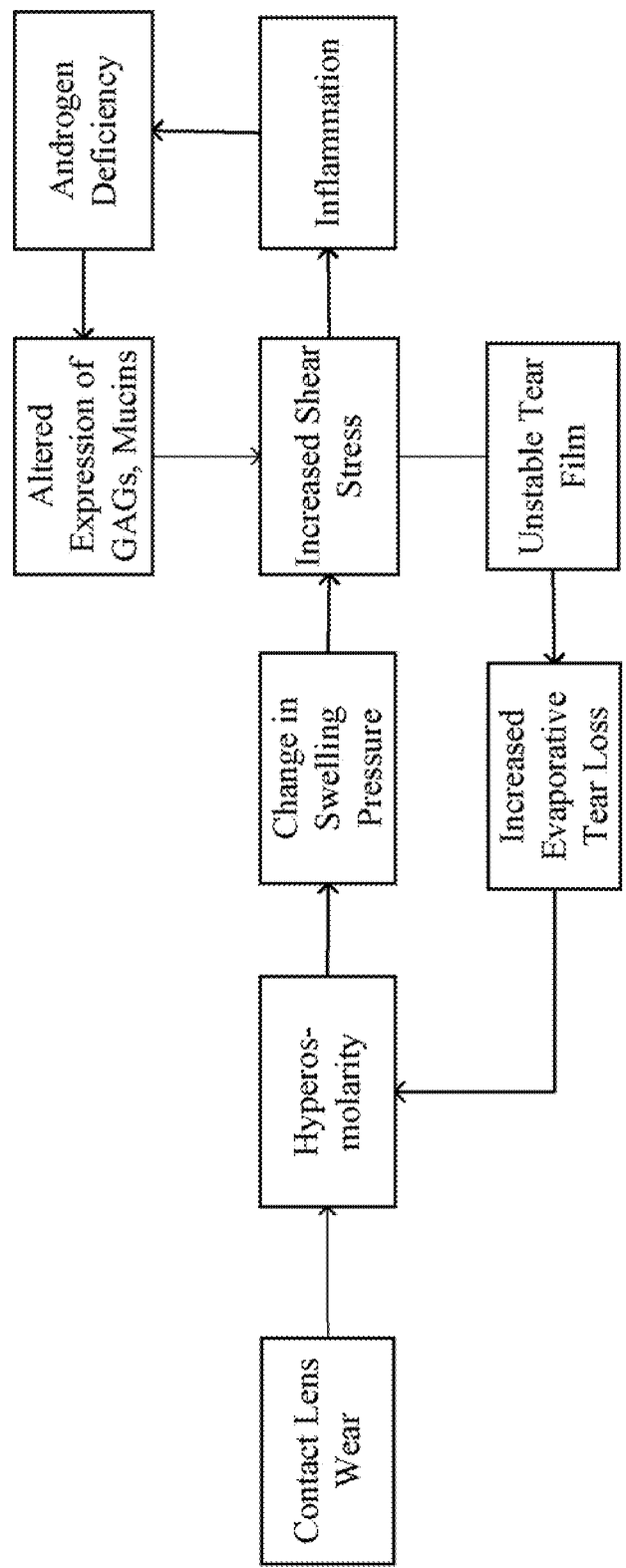
FIG. 1 represents feedback loops within ocular surface boundary lubrication.
Figure 2:
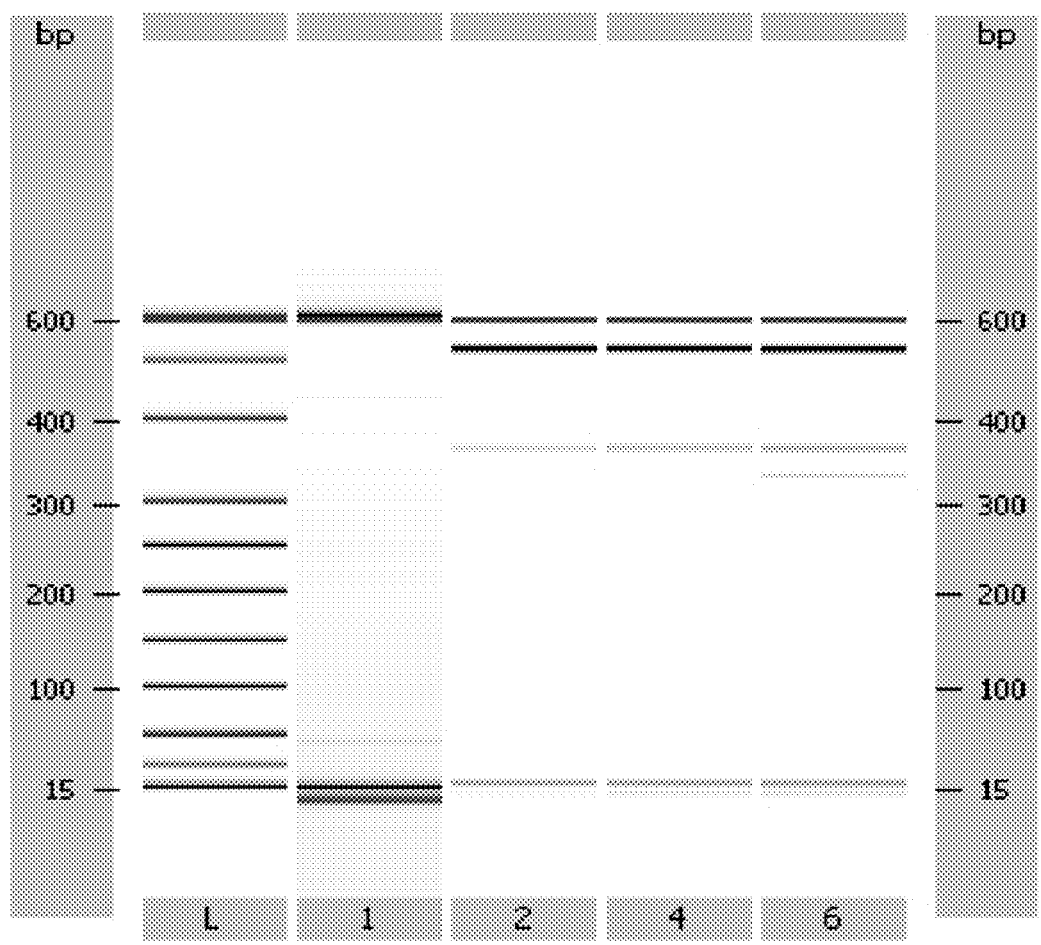
FIG. 2 illustrates PRG4 mRNA expression in human corneal epithelial cells. Human corneal epithelial cells were isolated from the corneoscleral rims of male and female donors. Amplified samples were screened for the presence of PRG4 products by using an Agilent 2100 Bioanalyzer. Vertical lanes contain: L. MW ladder; 1. No template control; 2. Corneal tissue from a 33-year female; 4. Cultured corneal epithelial cells from a 70-year female; 6. Cultured corneal epithelial cells from a 53-year male.
Figure 3:
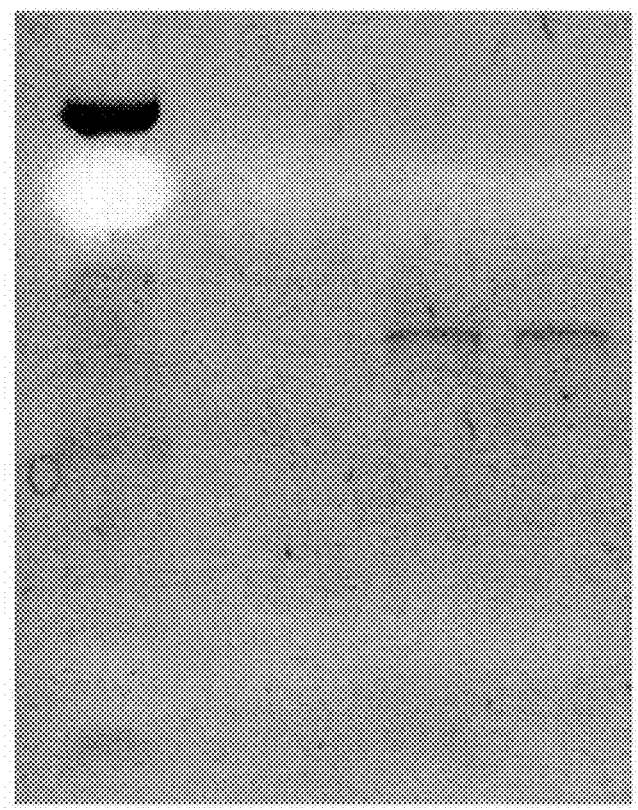
FIG. 3 illustrates PRG4 mRNA expression in human conjunctival epithelial cells. Human corneal epithelial cells were isolated from the corneoscleral rims of male and female donors. Amplified samples were screened for the presence of PRG4 products by using agarose gel electrophoresis. Vertical lanes contain: 1. MW ladder; 2. No template control; 4. Human female conjunctiva; 5. Human male conjunctiva.
Figure 4:
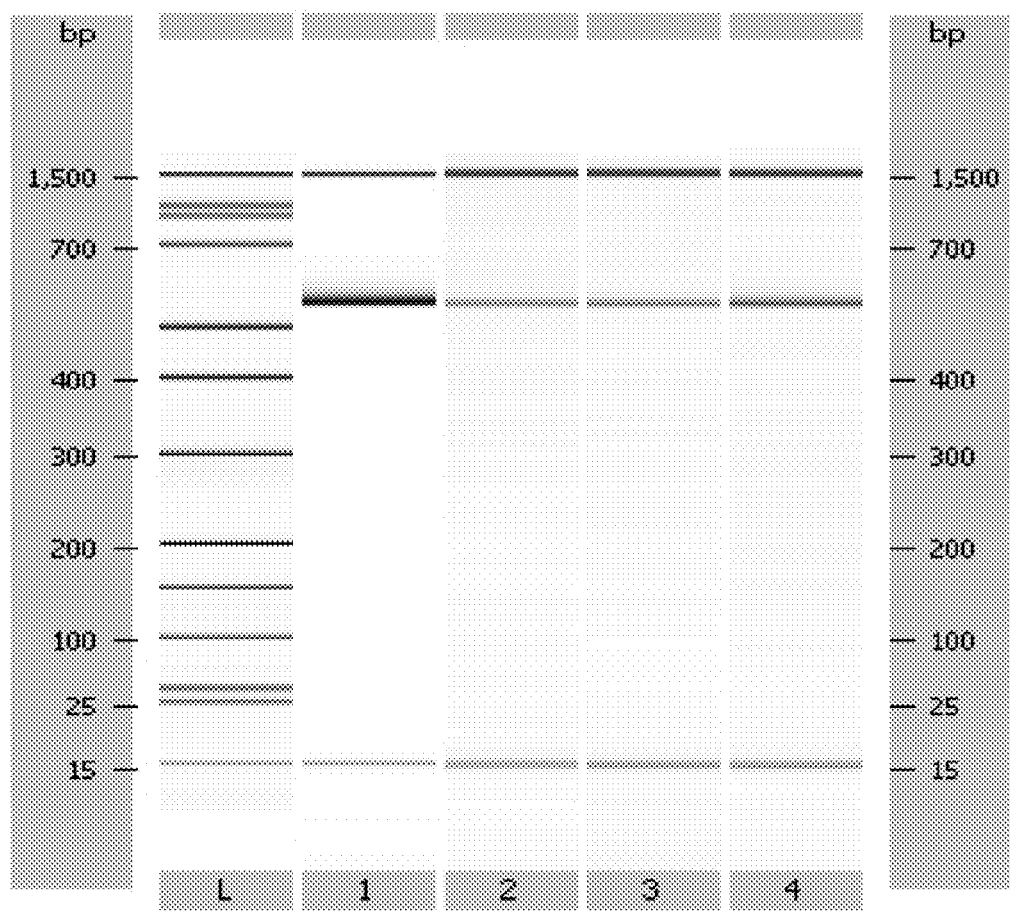
FIG. 4 illustrates PRG4 mRNA expression in human corneoscleral rim tissue samples. L. Human corneal epithelial cells were isolated from the corneoscleral rims of male and female donors. Amplified samples were screened for the presence of PRG4 products by using an Agilent 2100 Bioanalyzer. Vertical lanes contain: MW ladder; 1. Human liver cDNA standard; 2. Corneoscleral rim tissue from a 24-year female; 3. Corneoscleral rim tissue from a 51-year female; 4. Human conjunctival epithelial cells.
Figure 5:
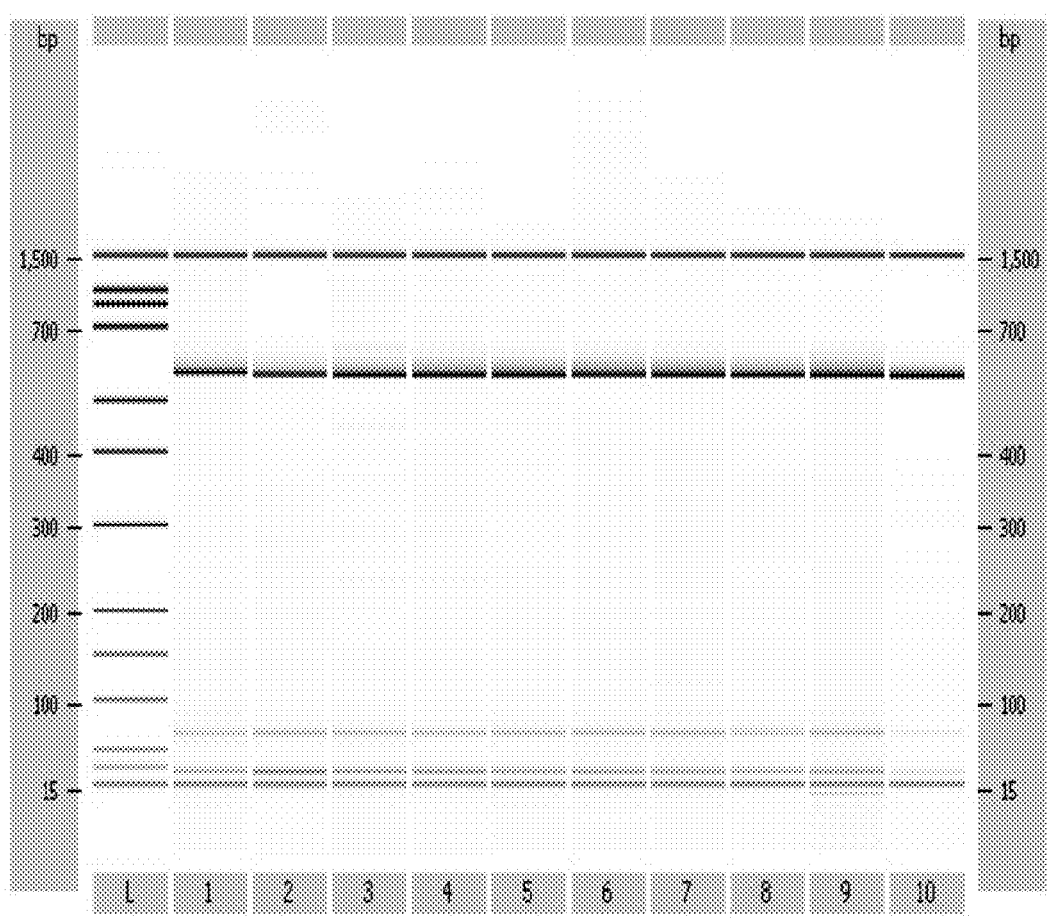
FIG. 5 illustrates PRG4 mRNA expression in human conjunctival impression cytology samples. Conjunctival impression cytology samples were isolated from male and female donors. Amplified samples were screened for the presence of PRG4 products by using an Agilent 2100 Bioanalyzer. Vertical lanes contain: L. MW ladder; 1-9. Conjunctival impression cytology samples; 10. Repeat of human conjunctival epithelial cells (Lane 4 in FIG. 3).

Though not wishing to be bound by theoretical mechanisms of action, as shown in FIG. 1, increased shear stress leads to tear film instability, evaporative tear loss, hyperosmolarity, changes in swelling pressure and a feedback elevation in shear stress. In some instances, increased shear stress promotes inflammation, androgen deficiency and decreased expression of proteoglycans. In certain instances increased shear stress and its sequelae may, over time, lead to a loss of boundary lubrication at the ocular surface. A deficiency in ocular lubrication and symptoms associated therewith can be determined by any suitable method. In some instances, a deficiency in ocular lubrication and symptoms associated therewith is defined either qualitatively (e.g., a feeling of low lubrication, dry eye, discomfort, etc.) or quantitatively (e.g., measured through mechanical, biochemical, electrical, optical or other methods of quantitative assays).

In certain instances, and as provided herein, PRG4 protein plays a critical role in the eye as a boundary lubricant. In some instances, this secreted glycoprotein protects the ocular surface to protect the cornea and conjunctiva against significant shear forces generated during an eyelid blink, contact lens wear, and any other undesirable ocular boundary lubrication caused by chronic inflammation and hyperosmolarity that result from dry eye disease, androgen deficiency, estrogen replacement therapy, compromised tear film, allergy, aging, ocular surface diseases, and increased protease levels in the tear film and at the ocular surface. Given the relationship between osmotic pressure and the electromechanical interactions within charged molecules, the present invention provides, in some embodiments, a pharmaceutical composition for managing a deficiency in ocular lubrication by modulating hyperosmolarity or osmolarity at the ocular surface via interrupting the feedback mechanisms that prevent secreted components from reducing friction coefficients and mitigating shear stress.

The present invention features a sacrificial mechanism for ocular boundary lubrication in association with ophthalmic lens wear, whereby surface bound receptors reversibly bind to a lubricating composition. In some embodiments, the lubricating composition comprises one or more gel forming and/or surfactant agents or compositions. In some instances, the gel forming or surfactant composition detach during a shear event, thereby preventing the shear stress from reaching (or reducing the shear stress reaching), the epithelial surface. In certain embodiments, following the transient shearing event, the gel forming and surfactant composition, allowed to return to their undisturbed equilibrium, rebind to the surface bound receptors. In some embodiments, the entire composition can detach during shear. In certain instances, that the thermodynamics of this equilibrium increase the probability of release from the receptor with increasing shear amplitude, but such that any one association is easily reversible.

Therefore, the current invention generally features a new approach to ocular lubrication in the presence of an ophthalmic lens. In particular, provided herein is a mechanism or process that relates to the use of a sacrificial mechanism to reduce friction at the interface between the ocular surface and an ophthalmic lens, including boundary lubricant molecules such as PRG4, hyaluronic acid, sodium hyaluronate, and phospholipids.

As used herein, an "ophthalmic lens" refers to lenses which are placed in intimate contact with the eye or tear fluid, such as contact lenses for vision correction (e.g., spherical, toric, bifocal), contact lenses for modification of eye color, ophthalmic drug delivery devices, ocular tissue protective devices (e.g., ophthalmic healing promoting lenses), and the like. A preferred ophthalmic lens is an extended-wear contact lens, especially extended-wear contact lenses for vision correction, with oxygen transmissibility or permeability, ion permeability, gas permeability, and other desirable transmissibility or permeability and features. As used herein, an "ocular environment" refers to ocular fluids (e.g., tear fluid) and ocular tissue (e.g., the cornea) which may come into intimate contact with a contact lens used for vision correction, drug delivery, wound healing, eye color modification, or other ophthalmic applications.

As used herein, an "outer surface" of an ophthalmic lens refers to the anterior surface of the lens which faces away from the eye during wear. The outer surface, which is typically substantially convex, may also be referred to as the front curve of the lens. The "inner surface" of a lens, as used herein, refers to the posterior surface of the lens which faces towards the eye during wear. The inner surface, which is typically substantially concave, may also be referred to as the base curve of the lens.

In one embodiment of the current invention, the sacrificial mechanism comprises a plurality of surface bound receptor comprising PRG4, and a lubricating composition reversibly bound to PRG4, wherein the lubricating composition comprises a gel forming composition comprising hyaluronic acid or sodium hyaluronate, or a surfactant composition comprising one or more surface active phospholipids, such as, L-α-dipalmitoylphosphatidylcholine, phosphatidylcholine, phosphatidylethanolamine, and sphingomyelin. In this embodiment, PRG4 is allowed to interact with endogenous proteins and proteoglycans within the tear film, and the exogenously supplied hyaluronic acid and/or phospholipids to establish a sacrificial mechanism to prevent protein or lipid adsorption at the lens surface, reduce dry spots on the lens, and reduce the friction between the lens and the ocular surface. In yet another feature of this embodiment, the hyaluronic acid and/or phospholipids are replenished in the form of a topical artificial tear drop, rewetting solution, contact lens cleaning products, an overnight incubation, or other contact lens care products.

As used herein, the terms "PRG4", "PRG4 protein" or "proteoglycan 4" and "lubricin" are used interchangeably. PRG4 is used herein also to encompass the term megakaryocyte stimulating factor (MSF), that has been accepted for the UCL/HGNC/HUGO Human Gene Nomenclature data base, and superficial zone protein (SZP). The PRG4 or lubricin protein as used herein refers to any isolated or purified native or recombinant lubricin proteins, homologs, functional fragments or motifs, isoforms, and/or mutants thereof. In certain embodiments, the isolated or purified PRG4 protein comprises an amino acid sequence for a human native or recombinant lubricin protein. In other embodiments, the isolated or purified PRG4 protein comprises an amino acid sequence encoded by prg4gene exons that encode the full length PRG4 protein or isoforms' primary structures. The proteoglycan 4 (prg4) gene contains 12 exons. The PRG4 protein used herein can comprise an amino acid sequence encoded by prg4gene exons 1-12, more preferably, exons 6-12, and most preferably, exons 9-12.

As used herein, the PRG4 protein includes any PRG4 proteins now known, or later described. In certain embodiments, a preferred PRG4 protein amino acid sequence is provided in SEQ ID NO: 1. The PRG4 protein shares the primary amino acid structure of any known PRG4 proteins or isoforms with at least 60% homology, preferably 75% homology, more preferably 85%, 90%, 95%, 96%, 97%, 98%, 99% or more homology. In certain embodiments, a preferred PRG4 protein has an average molar mass of between 50 kDa and 400 kDa, comprising one or more biological active portions of the PRG4 protein, or functional fragments, such as a lubricating fragment, or a homolog thereof.

In yet another embodiment, functional fragments, multimers (e.g., dimers, trimers, tetramers, etc.), homologs or orthologs of PRG4 act as the surface receptor and/or gel forming constructs in the sacrificial mechanism. Functional fragments and homologs of PRG4 include those with a fewer repeats within the central mucin-like KEPAPTT-repeat domain (SEQ ID NO:4), glycosylated and non-glycosylated forms of the protein, splice variants, recombinant forms, and the like. A lubricating fragment of PRG4 exhibits at least 20%, 30%, 40%, 50%, 60%, 70%, 80%, 90%, or 95% of the ophthalmic lubricating effect of human PRG4, as measured qualitatively, mechanically, optically, electrically, or by biochemical assay.

As used herein, the PRG4 protein comprises a biological active portion of the protein. As used herein, a "biologically active portion" of the PRG4 protein includes a functional fragment of a protein comprising amino acid sequences sufficiently homologous to, or derived from, the amino acid sequence of the protein, which includes fewer amino acids than the full length protein, and exhibits at least one activity of the full-length protein. Typically a biologically active portion comprises a functional domain or motif with at least one activity of the protein. A biologically active portion of a protein can be a polypeptide which is, for example, 10, 25, 50, 100, 200, or more amino acids in length. In one embodiment, a biologically active portion of the PRG4 protein can be used as a therapeutic agent alone or in combination with other therapeutic agents for treating undesirable or decreased ocular boundary lubrication.

The nucleic acid and amino acid sequences of several native and recombinant PRG4 or lubricin proteins, and characterization of the PRG4 proteins and various isoforms are disclosed in, for instance, U.S. Pat. Nos. 5,326,558; 6,433, 142; 7,030,223; 7,361,738 to Turner et al., and U.S. Pat. Nos. 6,743,774 and 6,960,562 to Jay et al. U.S. Publication No.

20070191268 to Flannery et al. also discloses recombinant PRG4 or lubricin molecules useful in the present invention.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and further transformed and expressed in a host cell for producing recombinant PRG4 protein.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising an active domain of the PRG4 gene and a nucleic acid sequence amplified using a primer of the invention.

In certain embodiments, the PRG4 protein encoding nucleic acid may contain one or more mutations, deletions, or insertions. In such embodiments, the PRG4 protein encoding nucleic acid is at least 60% homology, preferably 75% homology, more preferably 85%, 90%, 95%, 96%, 97%, 98%, 99%, or more homology, to a wild type PRG4 protein encoding nucleic acid.

As used herein, the term 'cDNAs' includes DNA that is complementary to mRNA molecules present in a cell or organism mRNA that can be convened into cDNA with an enzyme such as reverse transcriptase. In certain embodiments, the cDNA encoding PRG4 protein is isolated from PRG4 mRNA expressed in human corneal or conjunctival epithelial cells using an RT-PCR method well known in the art.

As used herein, the terms "polynucleotide," "nucleic acid/nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of thymine when the polynucleotide is RNA, instead of DNA. This alphabetical representation can be inputted into databases in a computer and used for bioinformatics applications such as, for example, functional genomics and homology searching.

As used herein, the term "isolated polynucleotide/cDNA" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule encoding the PRG4 protein used in the invention can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material, or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art. As used herein, a "native or naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In certain embodiments, the PRG4 protein used herein refers to PRG4 proteins or various homologs or isoforms thereof, that are naturally or recombinantly expressed in humans or other host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. "Genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" can be any cells that express a human PRG4 protein.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the PRG4 protein (e.g., SEQ ID NO:1).

As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of any known PRG4 proteins (e.g., SEQ ID NO:1), isoforms, or analogs thereof, and will exhibit a function similar to these peptides. As also Used herein, the term "paralogs" refers to two nucleic acids that are related by duplication within a genome. Paralogs usually have different functions, but these functions may be related.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of any known PRG4 protein (e.g., SEQ ID NO:1).

In certain embodiments, an isolated nucleic acid homolog encoding the PRG4 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such PRG4 protein (e.g., SEQ ID NO: 1).

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Furthermore, the PRG4 protein used herein includes PRG4 protein encoded by a polynucleotide that hybridizes to the polynucleotide encoding PRG4 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding PRG4 protein described herein. As used herein, the term "stringent conditions" refers to hybridization overnight at 60° C. in 10×Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10×Denhart's solution, 6×SSC, 0.5% SDS and 100 mg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are well known in the art. Accordingly, the PRG4 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human PRG4 protein (e.g., SEQ ID NO:1) or a specific isoform or homolog thereof.

Moreover, the PRG4 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In certain embodiments of the present invention, the chimeric protein is a chimera of PRG4 protein with other PRG4 protein isoforms.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In certain embodiments, the language "substantially free of cellular material" includes preparations of a PRG4 protein having less than about 30% (by dry weight) of other proteins (also referred to herein as a "contaminating protein"), more preferably less than about 20%, still more preferably less than about 10%, and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

In certain embodiments of the current invention, the surface bound receptors comprise hyaluronic acid. In this embodiment, the lubricating composition reversibly bound to the hyaluronic acid, wherein the lubricating composition comprises a gel forming composition comprising PRG4 and a surfactant composition comprising one or more surface active phospholipids, including but not limited to, L-α-dipalmitoylphosphatidylcholine, phosphatidylcholine, phosphatidylethanolamine, and sphingomyelin.

The present invention also provides an ophthalmic device comprising an ophthalmic lens with an outer surface and a inner surface and an ocular boundary lubricant composition disposed on at least a portion thereof one or more ocular boundary lubricant molecules selected from the group consisting of PRG4, a PGR4 inducer, hyaluronic acid, sodium hyaluronate, and a phospholipid, in an amount effective to provide ocular boundary lubrication in a patient wearing the ophthalmic lens.

As used herein, a "PRG4 inducing compound" or "PRG4 inducer" refers to a compound that increases the bioconcentration of PRG4, e.g., a compound that is capable of upregulating PRG4 expression, promoting the biosynthesis of PRG4, inhibiting degradation of PRG4, or the like, including but not limited to, an androgen or androgen analogue, selective androgen receptor modulator, selective estrogen receptor modulator, estrogen antagonist, aromatase inhibitor, antiprotease, proinflammatory cytokine antagonist (e.g. selected from the group consisting of anti-TNFα antibody, soluble TNFα receptor, and IL-1 receptor antagonist), cytokine release inhibitor, antiinflammatory cytokine (e.g. TGF-β), antiinflammatory agent (e.g. cyclosporine A, omega 3 and 6 fatty acids), NF-κ B inhibitor, or proteasome inhibitor, and pharmaceutically acceptable carriers for topical use.

In yet another embodiment, the androgen or androgen analogue is selected from the group consisting of a 17α-methyl-17β-hydroxy-2-oxa-5α-androstan-3-one derivative, a nitrogen-substituted androgen, a testosterone derivative, is a 4,5α-dihydrotestosterone derivative, a 19-nortestosterone derivative, a 17β-hydroxy-5α-androstane derivative containing a ring A unsaturation, and a structural subclass of androgens comprising androgenic compounds with unusual structural features.

In another preferred embodiment, the selective androgen receptor modulators (SARMs) are selected from a group consisting of aryl-propionamide (e.g. S-3-(4-acetylamino-phenoxy)-2-hydroxy-2-methyl-N-(4-nitro-3-trifluoromethyl-phenyl)-propionamide [S-4], or S-3-(4-fluorophenoxy)-2-hydroxy-2-methyl-N-(4-nitro-3-trifluoromethyl-phenyl)-propionamide [S-1]), bicyclic hydantoin, quinoline, and tetrahydroquinoline analogues that have in-vivo androgenic and anabolic activity of a non-steroidal ligand for the androgen receptor.

In yet another preferred embodiment, the selective estrogen receptor modulators (SERMs) are non-steroidal ligands of the estrogen receptor that are capable of inducing a number of conformational changes in the receptor and eliciting a variety of distinct biologic profiles. Preferably, the SERMs are those that prevent estrogen-induced inflammation in ocular surface tissues. In certain preferred embodiments, the estrogen antagonists are steroidal or non-steroidal compounds independent of receptor affinities.

Other molecules may also be used as surface bound receptors within the sacrificial mechanism of the current invention. For instance, DNA sequences recognizing gel forming or surfactant compositions (e.g., DNA aptamers), would serve as the surface bound receptor. These aptamers could recognize proteoglycans such as PRG4, hyaluronic acid, long chain sugars such as dextrans, polyethylene glycols, or other DNA constructs. The surface bound DNA could feature tunable affinity through an iterative evolutionary selection, or through ratiometric design against a semi-complementary hybrid (i.e., a purposefully mismatched polyG-A-polyG could act as a surface bound receptor for a polyG-T-polyG strand, with shortening lengths of polyG increasing relative affinity).

In certain embodiments, the surface bound receptors are adhered to the ophthalmic lens surface by direct adsorption, hydrophobic ionic, or covalent binding or by linker chemistries selected from the group consisting of homo- or hetero-bifunctional linkers, N-hydroxy succinimidyl esters, biotin, avidin, streptavidin, maleimide, thiol bonding, amines, hydrazones, dendrimers, and carbodiimides. Methods for disposing, adhering, coating, or attaching the surface bound receptors, or other desirable molecules, chemistries, monomers, oligomers, and polymers, to the ophthalmic lens are well known in the art.

In certain embodiments, the present invention provides that the gel forming or surfactant composition of the current invention further comprises one or more therapeutically effective amount or concentration of ophthalmically compatible and/or acceptable agents selected from the group consisting of an ophthalmically acceptable demulcent, excipient, astringent, vasoconstrictor, and emollient. As used herein, the term "ophthalmically compatible" refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of lipid adsorption, and will not cause substantial wearer discomfort during the prescribed period of wear.

As used herein, the term "effective concentration or amount" or "therapeutically effective concentration or amount" is intended to mean a nontoxic but sufficient concentration or amount to provide the desired therapeutic effects. The concentration or amount that is effective will vary from subject to subject, depending on the age and general condition of the individual, the particular agents, and the like. Thus, it is not always possible to specify an exact effective concentration or amount. However, an appropriate effective concentration or amount in any individual case may be determined by one of ordinary skill in the art using routine experimentation. Furthermore, the exact effective concentration or amount of the boundary lubricant molecules used herein and other therapeutic agent incorporated thereinto or dosage form of the present invention is not critical, so long as the concentration is within a range sufficient to permit ready application of the solution or formulation so as to deliver an amount of the boundary lubricant molecules and other active agents that is within a therapeutically effective range.

In certain embodiments, the pharmaceutically effective concentration of PRG4 protein is in a range of 10-10,000 µg/mL, preferably 50-5,00 mg/mL, and more preferably 100-300 mg/mL. As used herein, the ophthalmically acceptable agents comprising the ophthalmically acceptable demulcents, excipients, astringents, vasoconstrictors, and emollients that are fully defined in the Code of Federal Regulations 21CFR349.

In certain embodiments, the lubricating composition described herein comprises or the aforementioned ophthalmically acceptable agents are or can be combined with one or more of carboxymethylcellulose sodium (e.g., about 0.2 to about 2.5% w/v), hydroxyethyl cellulose (e.g., about 0.2 to about 2.5% w/v), hypromellose (e.g., about 0.2 to about 2.5% w/v), methylcellulose (e.g., about 0.2 to about 2.5% w/v), dextran 70 (e.g., about 0.1% w/v), gelatin (e.g., about 0.01% w/v), glycerin (e.g., about 0.2 to about 1% w/v), polyethylene glycol 300 (e.g., about 0.2 to about 1% w/v), polyethylene glycol 400 (e.g., about 0.2 to about 1% w/v), polysorbate 80 (e.g., about 0.2 to about 1% w/v), propylene glycol. (e.g., about 0.2 to about 1% w/v), polyvinyl alcohol (e.g., about 0.1 to about 4% w/v), povidone (e.g., about 0.1 to about 2% w/v), zinc sulfate (e.g., about 0.25% w/v), anhydrous lanolin (e.g., about 1 to about 10% w/v), lanolin (e.g., about 1 to about 10% w/v), light mineral oil (e.g., ≤about 50% w/v), mineral oil (e.g., ≤about 50% w/v), paraffin (e.g., ≤about 5% w/v), petrolatum (e.g., ≤about 100% w/v), white ointment (e.g., ≤about 100% w/v), white petrolatum (e.g., ≤about 100% w/v), white wax (e.g., ≤about 5% w/v), yellow wax (e.g., ≤about 5% w/v), ephedrine hydrochloride (e.g., about 0.123% w/v), naphazoline hydrochloride (e.g., about 0.01 to about 0.03% w/v), phenylephrine hydrochloride (e.g., about 0.08 to about 0.2% w/v), and tetrahydrozoline hydrochloride (e.g., about 0.01 to about 0.05% w/v). In certain instances, percent amounts utilized herein are percent amounts by weight.

In further embodiments, the therapeutically effective concentration of hyaluronic acid or sodium hyaluronate is in the range of 10-100,000 µg/mL, preferably 500-5,000 mg/mL, and the therapeutically effective concentration of the surface active phospholipids is in the range of 10-10,000 µg/mL, such surface active phospholipids include, but are not limited to, L-α-dipalmitoylphosphatidylcholine (DPPC), phosphatidylcholine (PC), phosphatidylethanolamine (PE) and sphingomyelin (Sp), or other neutral and polar lipids.

The lubricating composition as disclosed herein may further comprises one or more pharmaceutically acceptable carriers or vehicles comprising any acceptable materials, and/or any one or more additives known in the art. As used herein, the term "carriers" or "vehicle" refer to carrier materials suitable for topical drug administration. Carriers and vehicles useful herein include any such materials known in the art, which are nontoxic and do not interact with other components of the composition in a deleterious manner. Various additives, known to those skilled in the art, may be included in the composition. For example, solvents, including relatively small amounts of alcohol, may be used to solubilize certain drug substances. Other optional additives include opacifiers, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. Permeation enhancers and/or irritation-mitigating additives may also be included in the pharmaceutical composition of the present invention.

In certain embodiments, the pharmaceutically acceptable carrier comprises a phosphate buffered saline or an osmotically balanced salt solution of tear electrolytes, including one or more of sodium chloride in about 44% to about 54% mole fraction, potassium chloride in about 8% to about 14% mole fraction, sodium bicarbonate in about 8% to about 18% mole fraction, potassium bicarbonate in about 0% to about 4% mole fraction, calcium chloride in about 0% to about 4% mole fraction, magnesium chloride in about 0% to about 4% mole fraction, trisodium citrate in about 0% to about 4% mole fraction, and hydrochloric acid in about 0% to about 20% mole fraction or sodium hydroxide in about 0% to about 20% mole fraction. In certain embodiments, the pharmaceutical carrier can be formulated to generate an aqueous electrolyte solution in about 150-200 mM range. Other suitable formulations, such as ointments, creams, gels, pastes, and the like, suitable for topical administration, are also contemplated in the present invention. In certain embodiments, electrolytes provide proper osmotic balance when combined with PRG4 to make a solution ophthalmically acceptable.

The present invention further provides a method for providing ocular boundary lubrication to an individual in need thereof comprising applying to an eye of the individual an ophthalmic device comprising an ophthalmic lens with an outer surface and a inner surface and an ocular boundary lubricant composition disposed on at least a portion thereof one or more ocular boundary lubricant molecules selected from the group consisting of PRG4, a PGR4 inducer, hyaluronic acid, sodium hyaluronate, and a phospholipid, in an amount effective to provide ocular boundary lubrication in an individual wearing the ophthalmic lens. In one embodiment, the invention method is used for treating ocular surface hyperosmolarity in the individual who wear the ophthalmic lens. The invention method provides a sacrificial mechanism on the ophthalmic lens to mitigate shear stress, as discussed above.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Other features and advantages of the invention will be apparent from the following description of the preferred embodiments thereof and from the claims. These and many other variations and embodiments of the invention will be apparent to one of skill in the art upon a review of the appended description and examples.

EXAMPLES

Example 1

PRG4 mRNA Expression in Human Corneal and Conjunctival Epithelial Cells

Human corneal epithelial cells were isolated from the corneoscleral rims of male and female donors. Cells were processed either directly (n=8), or first cultured in phenol red-free keratinocyte serum free media (n=2). Bulbar conjunctivae (n=2), conjunctival impression cytology samples (n=9), immortalized human conjunctival epithelial cells after culture (n=1), NOD mouse lacrimal glands (n=5 adult mice/sex, 10 glands/sample), and BALB/c mouse meibomian glands (n=7 adult mice/sex, glands from 28 lids/sample) were obtained during surgical procedures. These samples were processed for the analysis of PRG4 mRNA by using primarily RT-PCR (n=18 human, all mouse) and Affymetrix GeneChips (n=4 human corneas). The PRG4 primers for PCR spanned over 1 kbp of intron sequences, in order to suppress amplification of contaminating chromosomal DNA (Table 1). Amplified samples were screened for the presence of PRG4 products by using agarose gel electrophoresis and an Agilent 2100 Bioanalyzer. To confirm the identity of amplicons, PCR products from cornea samples (n=2), conjunctival epithelial cells (n=1) and a human liver standard (n=1) were sequenced with a Genetic Analyzer at the Massachusetts Eye and Ear Infirmary DNA Sequencing Center for Vision Research (Boston, Mass.) and resulting data were analyzed with BLASTn searches of GenBank databases.

TABLE 1

Oligonucleotide primers designed for RT-PCR analysis of PRG4 mRNA

| Species | Orientation | Nucleotide sequence (5'-3') | Exons | Amplicon Size (bp) |
|---------|-------------|-----------------------------|-------|--------------------|
| Human | Sense | GATGCAGGGTACCCCAAA (SEQ ID NO: 2) | 9-12 | 526 |
|  | Antisense | CAGACTTTGGATAAGGTCTGCC (SEQ ID NO: 3) |  |  |

It was demonstrated that PRG4 mRNA is present in all human corneal and conjunctival epithelial cell and impression cytology samples. The identity of PRG4 PCR products was confirmed by DNA sequence analysis (Table 2). The results show that PRG4 is transcribed in human corneal and conjunctival epithelial cells.

TABLE 2

Identification of amplicon sequences from human cornea, conjunctival and liver samples

| | Sequencing Direction | Aligned Base Pairs To Human PRG4 | Total Base Pairs from Amplicon | BLASTn Search Identity |
|---|---|---|---|---|
| | | Human Liver Standard | | |
| A | Forward | 495 | 500 | Human PRG4 |
| A | Reverse | 488 | 491 | Human PRG4 |
| B | Forward | 496 | 499 | Human PRG4 |
| B | Reverse | 498 | 500 | Human PRG4 |
| | | Human Cornea (24 year old female) | | |
| A | Forward | 497 | 499 | Human PRG4 |
| A | Reverse | 490 | 492 | Human PRG4 |
| B | Forward | 500 | 504 | Human PRG4 |
| B | Reverse | 498 | 501 | Human PRG4 |
| | | Human Cornea (51 year old female) | | |
| A | Forward | 498 | 499 | Human PRG4 |
| A | Reverse | 474 | 489 | Human PRG4 |
| B | Forward | 496 | 498 | Human PRG4 |
| B | Reverse | 490 | 491 | Human PRG4 |
| | | Human Conjunctival Epithelial Cells | | |
| A | Forward | 496 | 499 | Human PRG4 |
| A | Reverse | 490 | 492 | Human PRG4 |

TABLE 2-continued

Identification of amplicon sequences from human cornea, conjunctival and liver samples

| | Sequencing Direction | Aligned Base Pairs To Human PRG4 | Total Base Pairs from Amplicon | BLASTn Search Identity |
|---|---|---|---|---|
| B | Forward | 495 | 499 | Human PRG4 |
| B | Reverse | 474 | 491 | Human PRG4 |

Two different samples (A & B) of each preparation were sequenced in forward and reverse directions. The human cornea samples were epithelial cells from the corneoscleral rims of female donors. The gene accession number for human PRG4 is NM_005807.

Example 2

Reduction of Friction In Vitro with the Addition of PRG4 (Lubricin)

An in vitro friction test with clinically relevant interfaces, such as an ocular surface-eyelid and ocular surface-contact lens interface is described below. Clinically relevant methods capable of quantitatively assessing the lubricating ability of artificial tears are currently lacking. Friction tests with synthetic (e.g. latex and glass) or non-ocular 'native' surfaces (e.g. umbilical cord vein segments) may facilitate some, but likely not all of the molecular interactions that occur during articulation/blinking. Indeed, the relevance of data obtained with non-tissue interfaces is unclear.

An annulus-on-disk rotational test configuration has been shown to be ideal for studying boundary lubrication at an articular cartilage-cartilage interface. A boundary mode of lubrication is indicated by kinetic friction being invariant with factors that influence formation of a fluid film, including sliding velocity and axial load. This is because surface-to-surface contact is occurring, and surface bound molecules contribute to lubrication (by decreasing friction and wear). Boundary lubrication has been discovered to be a critical and operative mechanism at the ocular surface, like it is at the articular cartilage surface. Therefore, the in vitro friction test previously developed and characterized to study boundary lubrication at an articular cartilage-cartilage interface was modified for the study of ocular surface-eye lid and ocular surface-contact lens interfaces.

To determine the test conditions in which boundary lubrication is dominant at the ocular surface-eyelid and ocular surface-contact lens interfaces, the dependence of frictional properties on axial load and sliding velocity was examined. Normal fresh human ocular surfaces (resected corneas with ~3 mm of sclera) were obtained from the Lions Eye Bank of Alberta. The resected corneas were stored in Optisol-GS at 4° C. and used within 2 weeks. Eyelids (age 60-80 years old) were obtained from the University of Calgary Body Donation Program within 1-3 days after death and used immediately or stored at −20° C. in saline for at most 2 weeks until use. Comparative lubricants consisted of Lens Plus Sterile Saline Solution (Advanced Medical Optics) as a negative control; Systane® Lubricant Eye props (Alcon Laboratories), Refresh Tears Lubricant Eye props (Allergan), Aquify® Long Lasting Comfort props (CIBA Vision) and Blink® Tears Lubricant Eye props (Advanced Medical Optics) as test lubricants.

Figure 6:
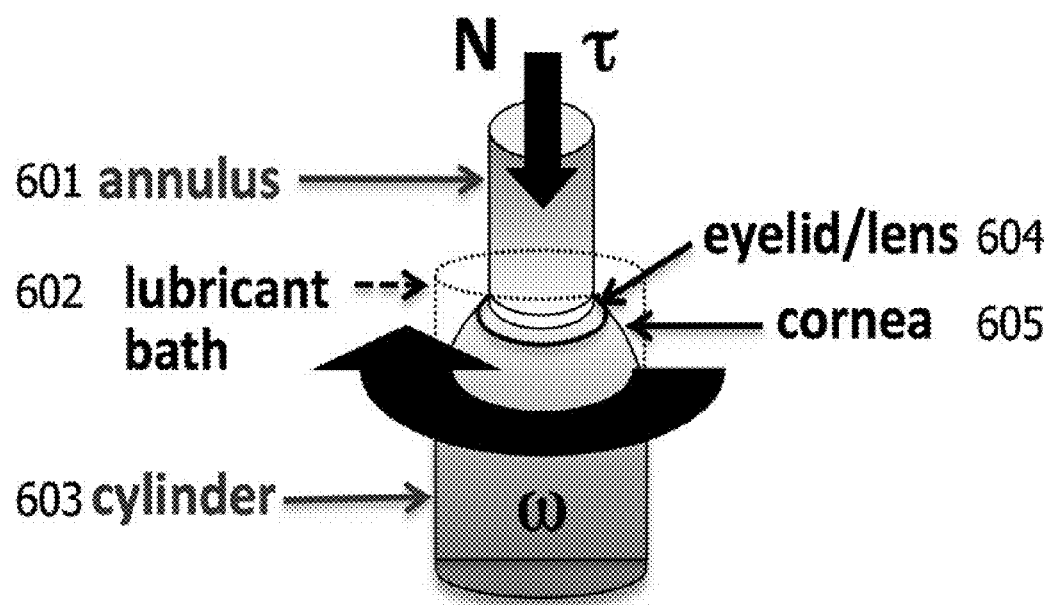
FIG. 6 illustrates a friction test schematic. The corneal ocular surface (605) was fastened to the spherical end of an inert non-permeable semi-rigid rubber plug cylinder (603) (radius r=6 mm). The plug cylinder (603) was attached to the rotational actuator of the mechanical testing machine (Bose ELF 3200) forming the bottom articular surface. An annulus (601) (outer radius=3.2 mm, inner radius=1.5 mm) was punched from the eyelid (604). The annulus (601) was attached to the linear actuator coupled with an axial load (N) and torsion (t) load cells, forming the upper articulating surface. Lubricant bath (602) was formed by securing an inert tube around the plug cylinder (603). ω is the angular frequency.

The friction test schematic is shown in FIG. 6. The corneal ocular surface (605) was fastened to the spherical end of an inert non-permeable semi-rigid rubber plug cylinder (603) (radius r=6 mm) by applying super glue to the sclera. This plug cylinder (603) was attached to the rotational actuator of the mechanical testing machine (BoseELF 3200) thus forming the bottom articular surface. An annulus (601) (outer radius=3.2 mm, inner radius=1.5 mm) was punched from the eyelid (604), and was attached to the linear actuator coupled with an axial load (N) and torsion ($\tau$) load cell, thus forming the upper articulating surface. Lubricant bath 602 was formed by securing an inert tube around the plug cylinder (603).

Samples were first tested in saline, then in one of the three (3) test lubricants. The lubricant bath was filled with ~0.3 ml, and the articulating surfaces allowed to equilibrate with the lubricant. The sample surfaces were slowly (0.05 mm/s) brought into contact and compressed until the spherical plug flattened out and the entire annular eyelid surface was in contact with the cornea (605). The resulting normal stress (calculated from axial load as, in units of MPa, as N/($\pi$ [$r^2_{outer} - r^2_{inner}$]) can be varied by using different stiffness rubber plugs to mimic physiological stresses ~5 kPa. The test sequence was initiated by preconditioning the sample by rotating +4 revolutions (rev) and reset with −4 revolutions at a physiologically relevant effective linear sliding velocity, veff=30 mm/s (where veff=$\omega$Reff, $\omega$ is the angular frequency, and Reff=2.4 mm is the effective radius calculated by integrating the shear stress distribution over the annular contact area). Samples were then tested by rotating +4 revolutions, immediately followed by −4 reset revolutions at veff=30, 10, 1, 0.3 and then 30 mm/s, with a dwell time of 12 second between each revolution. The test sequence was then be repeated in the opposite direction of rotation.

To evaluate the lubrication properties of the ocular surface, two friction coefficients ($\mu$) of the form $\mu=\tau/(R_{eff}N)$ where is torque, $R_{eff}$ is effective radius, and N is axial load, described above. A static friction coefficient, which reflects the resistance to the onset of motion, $\mu_{static}$ was calculated as the peak value of $\mu$, just after (within)~10° the start of rotation. An average kinetic friction coefficient, which reflects the resistance to steady state motion, $<\mu_{kinetic}>$ was calculated from p averaged during the third and fourth complete test revolution. Both $\mu_{static}$ and $<\mu_{kinetic}>$ were averaged for the + and − revolutions in each test to account for potential directional effects on $\tau$ measurements. Data was collected at a frequency of 20 Hz.

Figure 7:
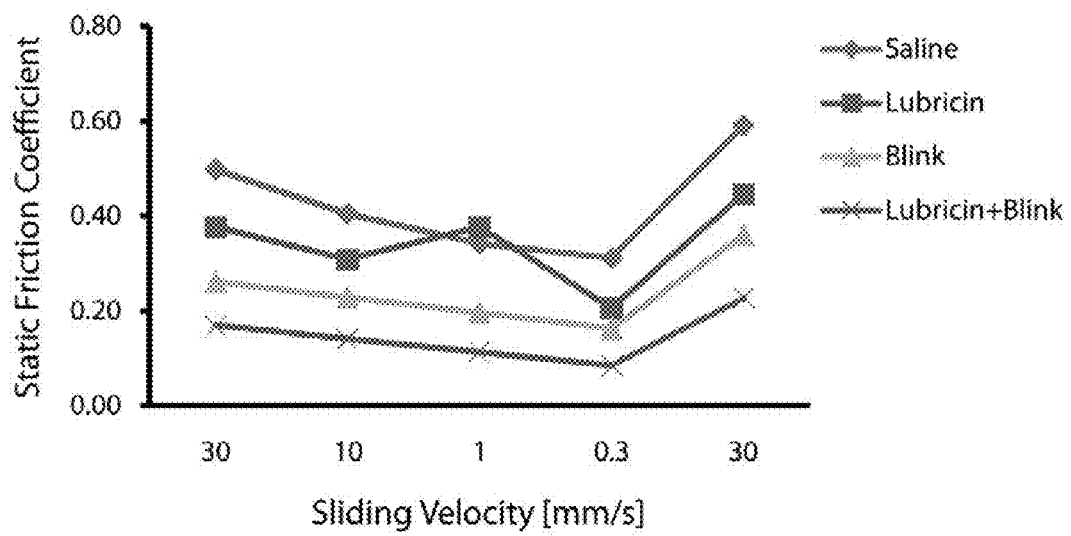
FIG. 7 illustrates the reduction of in vitro lid/cornea kinetic friction with addition of PRG4 protein (lubricin).
Figure 7:
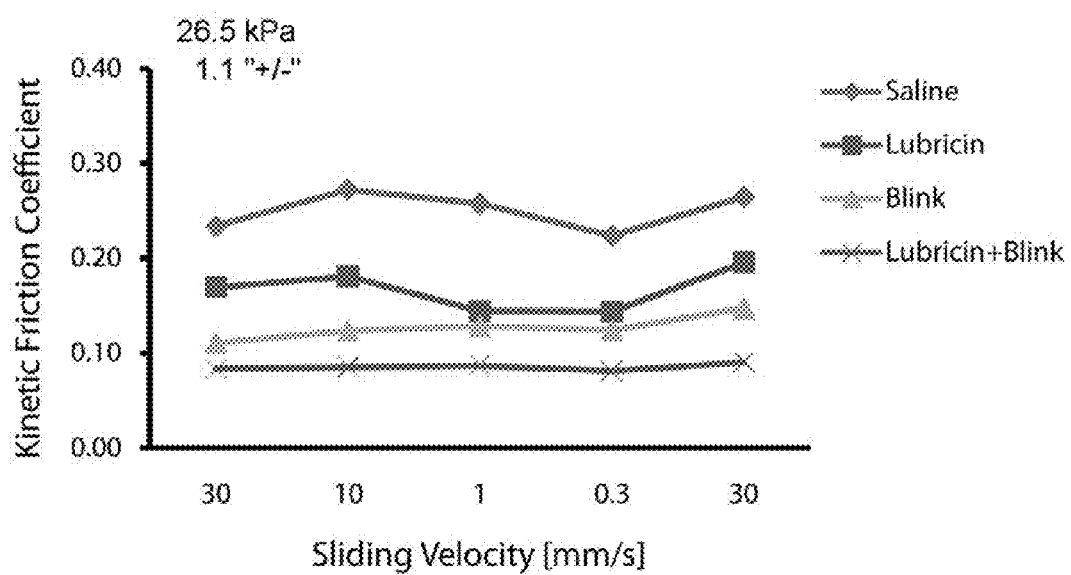

The results of lubricin (PRG4) added to the corneal surface at a concentration in the range of 100-300 ug/mL are shown in FIG. 7. Lubricin had a friction lowering effect at the eyelid interface, both in terms of kinetic and static friction, at all velocities. At a concentration 1/10th of that of physiological hyaluronic acid, lubricin was similar to Blink® Tears Lubricant Eye props, which contains hyaluronic acid. In combination, the two lubricants are better than either alone.

Figure 8:
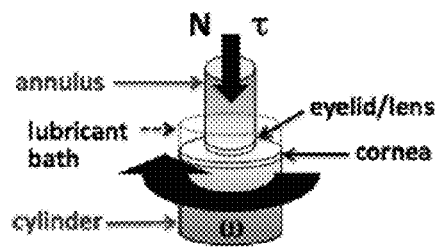
FIG. 8 illustrates the reduction of in vitro lid/cornea kinetic friction measured 1 minute after the addition of PRG4 protein (lubricin).
Figure 8:
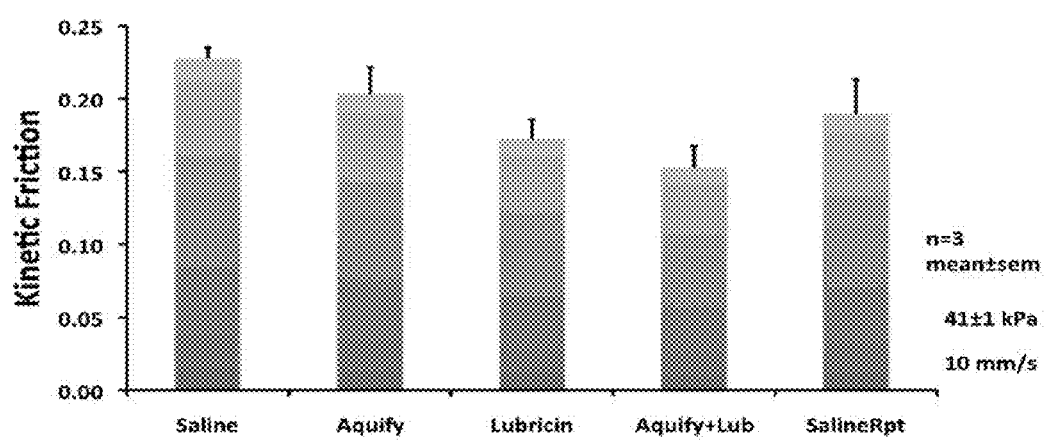

FIG. 8 demonstrates the reduction of in vitro cornea/lid kinetic friction measured during the first minute after the addition of lubricin, as compared to Aquify® eye drops. Lubricants were thoroughly washed from the ocular surface using saline between tests. A synergistic effect (reduced $\mu_{kinetic}$ over either alone) was evident when Aquify® (with hyaluronic acid) was combined with lubricin. The saline repeat was lower than the original saline control. This showed a retention of lubricin's effect even after washing with saline, suggesting that the molecules were binding to the ocular surface, and that lubricin demonstrated superior retention time as compared to sodium hyaluronate alone.

Figure 9:
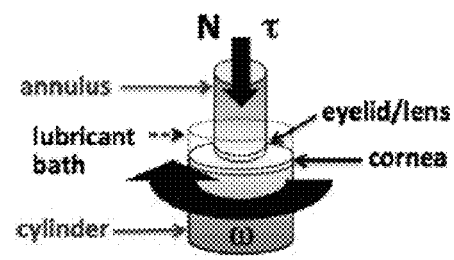
FIG. 9 illustrates the reduction of in vitro lid/cornea kinetic friction measured 5 minutes after the addition of PRG4 protein (lubricin).
Figure 9:
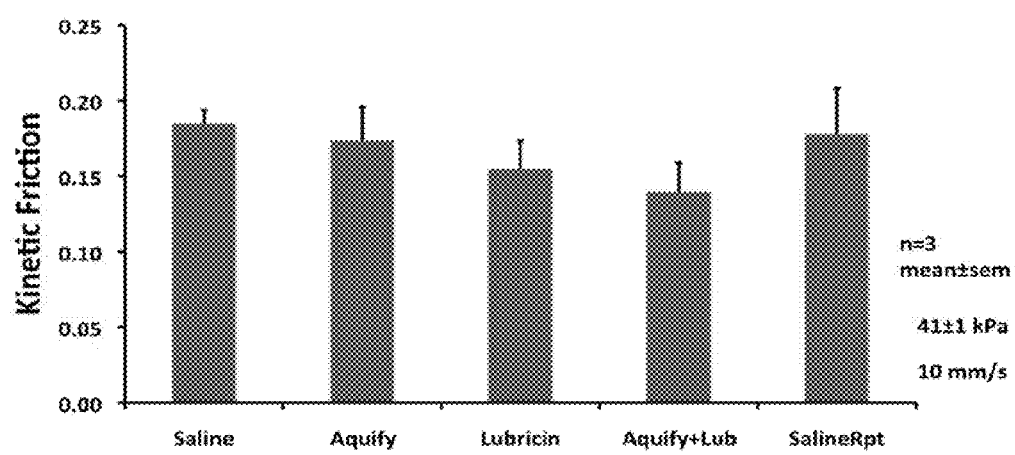

FIG. 9 demonstrates the reduction of in vitro cornea/lid kinetic friction measured during the 5th minute after the addition of lubricin, as compared to Aquify® eye drops. A synergistic effect (reduced $\mu_{kinetic}$ over either alone) was evident when Aquify® (with hyaluronic acid) was combined with lubricin. The friction coefficient of Aquify® had returned to statistical equivalence to saline after 5 minutes, whereas lubricin remains lower, as did the combination of lubricin and hyaluronic acid.

Figure 10:
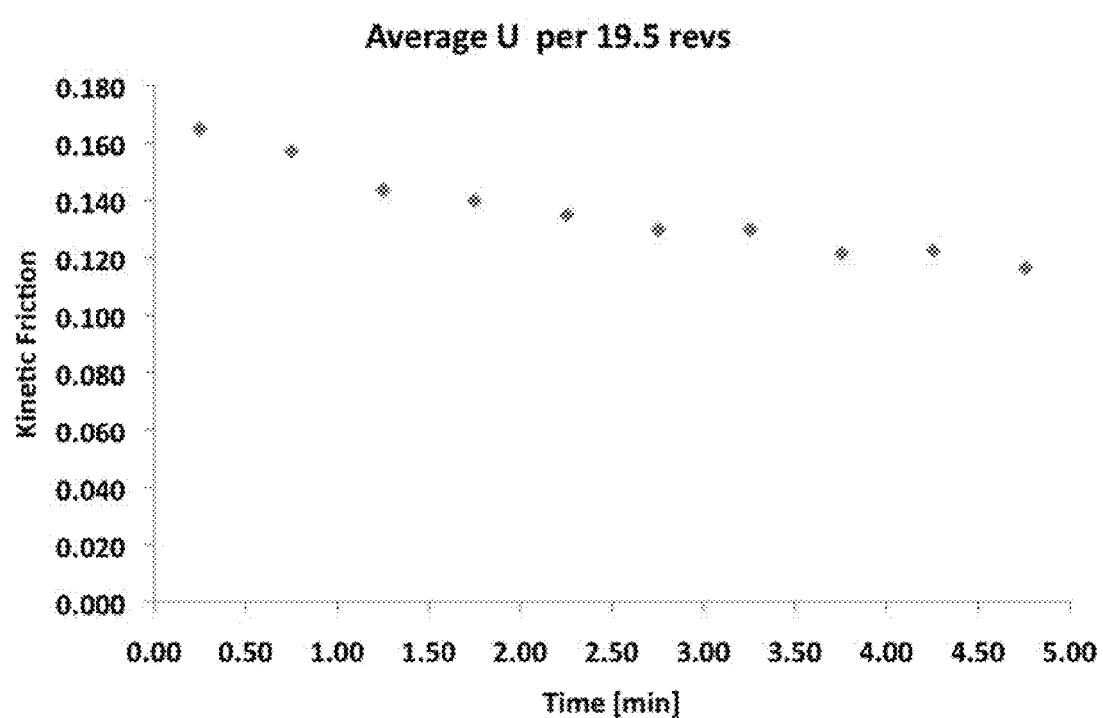
FIG. 10 illustrates the reduction of in vitro lid/cornea kinetic friction over time, following addition of PRG4 protein (lubricin).

FIG. 10 shows the reduction of kinetic friction coefficient over time, following addition of lubricin. Again, the continual reduction suggested binding to the ocular surface.

REFERENCES

1. G. D. Jay, Cum Opin Orthop 15, 355 (2004).
2. Schumacher B L, Hughes C E, Kuettner K E, Caterson B, Aydelotte M B. Immunodetection and partial cDNA sequence of the proteoglycan, superficial zone protein, synthesized by cells lining synovial joints. J Orthop Res. 1999 January; 17(1):110-20.
3. S. G. Rees et al., Matrix Biology 21, 593 (2002).
4. Schumacher B L, Schmidt T A, Voegtline M S, Chen A C, Sah R L. Proteoglycan 4 (PRG4) synthesis and immunolocalization in bovine meniscus. J Orthop Res. 2005 May; 23(3):562-8.
5. J. Marcelino et al., Nat Genet. 23, 319 (1999).
6. D. K. Rhee et al., J Clin Invest 115, 622 (2005).
7. Cutolo M, Capellino S, Sulli A, Serioli B, Secchi M E, Villaggio B, Straub R H. Estrogens and autoimmune diseases. Ann NY Acad Sci 2006; 1089:538-547.
8. Cutolo M, Sulli A, Capellino S, Villaggio B, Montagna P, Pizzorni C, Paolino S, Seriolo B, Felli L, Straub R H. Anti-TNF and sex hormones. Ann NY Acad Sci 2006; 1069:391-400.
9. Rontzsch A, Thoss K, Petrow P K, Henzgen S, Brauer R. Amelioration of murine antigen-induced arthritis by dehydroepiandrosterone (DHEA). Inflamm Res 2004; 53:189-198.
10. Schwarz I M, Hills B A, Br. J. Rheum. 1998; 37:21-26.
11. Jay G D, Hong B S. Connect Tissue Res, 1992; 28(1-2): 89-98.
12. Jones M B. et. al. Mathematical Medicine and Biology 2005; 22, 265.
13. E. Meyer, R. M. Overney, K. Dransfeld, T. Gyalog, Nanoscience: Friction and Rheology on the Nanometer Scale (World Scientific Publishing Co. Pte. Ltd, River Edge, N.J., 2002), pp. 373.
14. D. Dowson, Proc Inst Mech Eng [H] 215, 335 (2001).
15. G. A. Ateshian, V. C. Mow, in Basic Orthopaedic Biomechanics and Mechano-Biology V. C. Mow, R. Huiskes, Eds. (Lippincott Williams & Wilkins, Philadelphia, 2005) pp. 447-494.
16. F. Guilak, Arthritis Rheum 52, 1632 (June, 2005).
17. K. C. Morell, W. A. Hodge, D. E. Krebs, R. W. Mann, Proc Natl Acad Sci USA 102, 14819 (Oct. 11, 2005).
18. S. A. V. Swanson, in Adult Articular Cartilage M. A. R. Freeman, Ed. (Pitman Medical, Tunbridge Wells, England, 1979) pp. 415-460.
19. K. C. Morrell, W. A. Hodge, D. E. Krebs, R. W. Mann, Proc Natl Acad Sci USA 102, 14819 (Oct. 11, 2005).
20. C. W. McCutchen, Fed Proceedings 25, 1061 (1966).
21. T. Murakami, Y. Sawae, M. Ihara, JSME Int J Series C-Mechanical Systems Machine Elements & Manufacturing 46, 594 (2003).
22. G. Meachim, Ann Rheum Dis 31, 457 (1972).
23. Schmidt M, Naumann H, Weidler C, Schellenberg M, Anders S, Straub R H. Inflammation and sex hormone metabolism. Ann NY Acad Sci 2006; 1069:236-246.
24. Luensmann D, Jones L, Contact Lens & Anterior Eye 2008; 31, 179ification of dry eye disease: report of the Definition and Classification Subcommittee of the International Dry Eye WorkShop (2007). Ocular Surface. 2007 April; 5(2):75-92.
25. Subbaraman L N, Glasier M A, Senchyna M, Sheardown H, Jones L. Eye Contact Lens. 2007 July; 33(4):169-73.

What is claimed is:

1. An ophthalmic device comprising an ophthalmic lens with an outer surface and an inner surface and a lubricating composition comprising proteoglycan 4 (PRG4) disposed on at least a portion of the outer or inner surface in an amount effective to provide ocular boundary lubrication in an ocular environment of an individual wearing the ophthalmic lens, and wherein the PRG4 is bound to said surface.

2. The ophthalmic device of claim 1, wherein the lubricating composition further comprises at least one gel forming agent, a surfactant, or a combination thereof associated with said PRG4.

3. The ophthalmic device of claim 2, wherein the lubricating composition comprises at least one gel forming agent comprising hyaluronic acid, sodium hyaluronate, or a combination thereof.

4. The ophthalmic device of claim 2, wherein the surfactant comprises one or more surface active phospholipids.

5. The ophthalmic device of claim 4, wherein the surface active phospholipid is selected from the group consisting of L-α-dipalmitoylphosphatidylcholine, phosphatidylcholine, phosphatidylethanolamine, and sphingomyelin.

6. The ophthalmic device of claim 1, wherein the PRG4 has an average molar mass of between 50 kDa and 400 kDa, and comprises recombinant PRG4, isolated naturally occurring PRG4, or a lubricating fragment thereof.

7. The ophthalmic device of claim 1, wherein the PRG4 is bound to the ophthalmic lens surface by direct adsorption, hydrophobic ionic binding, covalent binding or by linker chemistries selected from the group consisting of homo- or hetero-bifunctional linkers, N-hydroxy succinimidyl esters, biotin, avidin, streptavidin, maleimide, thiol bonding, amines, hydrazones, dendrimers, and carbodiimides.

8. The ophthalmic device of claim 1, wherein the lubricating composition further comprises one or more ophthalmically acceptable agents selected from the group consisting of an ophthalmically acceptable demulcent, an ophthalmically acceptable excipient, an ophthalmically acceptable astringent, an ophthalmically acceptable vasoconstrictor, an ophthalmically acceptable emollient, and tear electrolytes.

9. A method for providing ocular boundary lubrication to an individual in need thereof, comprising applying to an eye of the individual an ophthalmic device comprising an ophthalmic lens with an ocular boundary lubricant composition disposed on at least a portion thereof and comprising PRG4 in an amount effective to provide ocular boundary lubrication in an ocular environment in the individual.

10. The method of claim 9, wherein the individual is in need of treatment for ocular surface hyperosmolarity.

11. The ophthalmic device of claim 1, wherein the ophthalmic lens is a contact lens.

12. The ophthalmic device of claim 7, wherein the ophthalmic lens is a contact lens.

13. The method of claim 9, wherein the ophthalmic lens is a contact lens.

* * * * *

UNITED STATES PATENT AND TRADEMARK OFFICE
CERTIFICATE OF CORRECTION

PATENT NO. : 8,563,028 B2
APPLICATION NO. : 12/940454
DATED : December 3, 2013
INVENTOR(S) : Sullivan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 137 days.

Signed and Sealed this
Twenty-fourth Day of February, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,563,028 B2
APPLICATION NO. : 12/940454
DATED : October 22, 2013
INVENTOR(S) : Benjamin Sullivan, Tannin A. Schmidt and David A. Sullivan It is certified that error appears in the above-identified patent and that said Letters Patent is hereby corrected as shown below:

In the Specification

Please replace Column 1, Line 16 with the following:
--This invention was made with government support under EY005612 awarded by the National Institutes of Health. The government has certain rights in the invention.--

Signed and Sealed this
Ninth Day of May, 2023

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Pro Ser Gly Ala Ser Gln Thr
```

```
                115                 120                 125
Ile Lys Ser Thr Thr Lys Arg Ser Pro Lys Pro Asn Lys Lys
130                 135                 140

Thr Lys Lys Val Ile Glu Ser Glu Ile Thr Glu His Ser Val
145                 150                 155                 160

Ser Glu Asn Gln Glu Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
                195                 200                 205

Lys Lys Lys Pro Thr Pro Lys Pro Val Val Asp Glu Ala Gly Ser
210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
                260                 265                 270

Glu Thr Ser Leu Thr Val Asn Lys Glu Thr Thr Val Glu Thr Lys Glu
                275                 280                 285

Thr Thr Thr Thr Asn Lys Gln Thr Ser Thr Asp Gly Lys Glu Lys Thr
                290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
                340                 345                 350

Thr Thr Pro Lys Glu Pro Ala Ser Thr Thr Pro Lys Glu Pro Thr Pro
                355                 360                 365

Thr Thr Ile Lys Ser Ala Pro Thr Thr Pro Lys Glu Pro Ala Pro Thr
                370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
                420                 425                 430

Lys Glu Pro Ala Pro Thr Thr Pro Lys Lys Pro Ala Pro Thr Thr Pro
                435                 440                 445

Lys Glu Pro Ala Pro Thr Thr Pro Lys Glu Pro Thr Pro Thr Thr Pro
                450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
                500                 505                 510

Glu Pro Ser Pro Thr Thr Pro Lys Glu Pro Ala Pro Thr Thr Thr Lys
                515                 520                 525

Ser Ala Pro Thr Thr Thr Lys Glu Pro Ala Pro Thr Thr Thr Lys Ser
530                 535                 540
```

-continued

```
Ala Pro Thr Thr Pro Lys Glu Pro Ser Pro Thr Thr Lys Glu Pro
545                 550                 555                 560
Ala Pro Thr Thr Pro Lys Glu Pro Ala Pro Thr Thr Pro Lys Pro
                565                 570                 575
Ala Pro Thr Thr Pro Lys Glu Pro Ala Pro Thr Thr Pro Lys Glu Pro
                580                 585                 590
Ala Pro Thr Thr Pro Lys Lys Pro Ala Pro Thr Thr Pro Lys Glu Pro
                595                 600                 605
Ala Pro Thr Thr Pro Lys Glu Thr Ala Pro Thr Thr Pro Lys Lys Leu
610                 615                 620
Thr Pro Thr Thr Pro Glu Lys Leu Ala Pro Thr Thr Pro Glu Lys Pro
625                 630                 635                 640
Ala Pro Thr Thr Pro Glu Glu Leu Ala Pro Thr Thr Pro Glu Glu Pro
                645                 650                 655
Thr Pro Thr Thr Pro Glu Glu Pro Ala Pro Thr Thr Pro Lys Ala Ala
                660                 665                 670
Ala Pro Asn Thr Pro Lys Glu Pro Ala Pro Thr Thr Pro Lys Glu Pro
                675                 680                 685
Ala Pro Thr Thr Pro Lys Glu Pro Ala Pro Thr Thr Pro Lys Glu Thr
                690                 695                 700
Ala Pro Thr Thr Pro Lys Gly Thr Ala Pro Thr Thr Leu Lys Glu Pro
705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Cys Asp Lys Pro Ala Pro Thr
                740                 745                 750
Thr Pro Lys Gly Thr Ala Pro Thr Thr Pro Lys Glu Pro Ala Pro Thr
                755                 760                 765
Thr Pro Lys Glu Pro Ala Pro Thr Thr Pro Lys Gly Thr Ala Pro Thr
                770                 775                 780
Thr Leu Lys Glu Pro Ala Pro Thr Thr Pro Lys Lys Pro Ala Pro Lys
785                 790                 795                 800
Glu Leu Ala Pro Thr Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
                820                 825                 830
Glu Pro Ala Pro Thr Thr Pro Lys Lys Pro Ala Pro Thr Thr Pro Glu
                835                 840                 845
Thr Pro Pro Pro Thr Thr Ser Glu Val Ser Thr Pro Thr Thr Thr Lys
                850                 855                 860
Glu Pro Thr Thr Ile His Lys Ser Pro Asp Glu Ser Thr Pro Glu Leu
865                 870                 875                 880
Ser Ala Glu Pro Thr Pro Lys Ala Leu Glu Asn Ser Pro Lys Glu Pro
                885                 890                 895
Gly Val Pro Thr Thr Lys Thr Pro Ala Ala Thr Lys Pro Glu Met Thr
                900                 905                 910
Thr Thr Ala Lys Asp Lys Thr Thr Glu Arg Asp Leu Arg Thr Thr Pro
                915                 920                 925
Glu Thr Thr Thr Ala Ala Pro Lys Met Thr Lys Glu Thr Ala Thr Thr
                930                 935                 940
Thr Glu Lys Thr Thr Glu Ser Lys Ile Thr Ala Thr Thr Gln Val
945                 950                 955                 960
Thr Ser Thr Thr Thr Gln Asp Thr Thr Pro Phe Lys Ile Thr Thr Leu
                965                 970                 975
```

-continued

```
Lys Thr Thr Thr Leu Ala Pro Lys Val Thr Thr Lys Lys Thr Ile
            980                 985                 990

Thr Thr Thr Glu Ile Met Asn Lys Pro Glu Glu Thr Ala Lys Pro Lys
            995                 1000                1005

Asp Arg Ala Thr Asn Ser Lys Ala Thr Thr Pro Lys Pro Gln Lys
            1010                1015                1020

Pro Thr Lys Ala Pro Lys Lys Pro Thr Ser Thr Lys Lys Pro Lys
            1025                1030                1035

Thr Met Pro Arg Val Arg Lys Pro Lys Thr Thr Pro Thr Pro Arg
            1040                1045                1050

Lys Met Thr Ser Thr Met Pro Glu Leu Asn Pro Thr Ser Arg Ile
            1055                1060                1065

Ala Glu Ala Met Leu Gln Thr Thr Thr Arg Pro Asn Gln Thr Pro
            1070                1075                1080

Asn Ser Lys Leu Val Glu Val Asn Pro Lys Ser Glu Asp Ala Gly
            1085                1090                1095

Gly Ala Glu Gly Glu Thr Pro His Met Leu Leu Arg Pro His Val
            1100                1105                1110

Phe Met Pro Glu Val Thr Pro Asp Met Asp Tyr Leu Pro Arg Val
            1115                1120                1125

Pro Asn Gln Gly Ile Ile Ile Asn Pro Met Leu Ser Asp Glu Thr
            1130                1135                1140

Asn Ile Cys Asn Gly Lys Pro Val Asp Gly Leu Thr Thr Leu Arg
            1145                1150                1155

Asn Gly Thr Leu Val Ala Phe Arg Gly His Tyr Phe Trp Met Leu
            1160                1165                1170

Ser Pro Phe Ser Pro Pro Ser Pro Ala Arg Arg Ile Thr Glu Val
            1175                1180                1185

Trp Gly Ile Pro Ser Pro Ile Asp Thr Val Phe Thr Arg Cys Asn
            1190                1195                1200

Cys Glu Gly Lys Thr Phe Phe Phe Lys Asp Ser Gln Tyr Trp Arg
            1205                1210                1215

Phe Thr Asn Asp Ile Lys Asp Ala Gly Tyr Pro Lys Pro Ile Phe
            1220                1225                1230

Lys Gly Phe Gly Gly Leu Thr Gly Gln Ile Val Ala Ala Leu Ser
            1235                1240                1245

Thr Ala Lys Tyr Lys Asn Trp Pro Glu Ser Val Tyr Phe Phe Lys
            1250                1255                1260

Arg Gly Gly Ser Ile Gln Gln Tyr Ile Tyr Lys Gln Glu Pro Val
            1265                1270                1275

Gln Lys Cys Pro Gly Arg Arg Pro Ala Leu Asn Tyr Pro Val Tyr
            1280                1285                1290

Gly Glu Thr Thr Gln Val Arg Arg Arg Phe Glu Arg Ala Ile
            1295                1300                1305

Gly Pro Ser Gln Thr His Thr Ile Arg Ile Gln Tyr Ser Pro Ala
            1310                1315                1320

Arg Leu Ala Tyr Gln Asp Lys Gly Val Leu His Asn Glu Val Lys
            1325                1330                1335

Val Ser Ile Leu Trp Arg Gly Leu Pro Asn Val Val Thr Ser Ala
            1340                1345                1350

Ile Ser Leu Pro Asn Ile Arg Lys Pro Asp Gly Tyr Asp Tyr Tyr
            1355                1360                1365

Ala Phe Ser Lys Asp Gln Tyr Tyr Asn Ile Asp Val Pro Ser Arg
```

```
                1370              1375              1380
Thr Ala  Arg Ala Ile Thr Thr  Arg Ser Gly Gln Thr  Leu Ser Lys
         1385              1390              1395

Val Trp  Tyr Asn Cys Pro
         1400

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgcagggt accccaaa                                                 18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagactttgg ataaggtctg cc                                            22

<210> SEQ ID NO 4
<211> LENGTH: 7
<212> TYPE: PRT
<213> ORGANISM: Homo sapiens

<400> SEQUENCE: 4

Lys Glu Pro Ala Pro Thr Thr
1                5
```